(12) United States Patent
Truckai

(10) Patent No.: US 12,114,836 B2
(45) Date of Patent: Oct. 15, 2024

(54) DEFLECTABLE ENDOSCOPE AND METHOD OF USE

(71) Applicant: Meditrina, Inc., San Jose, CA (US)

(72) Inventor: Csaba Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 91 days.

(21) Appl. No.: 18/159,599

(22) Filed: Jan. 25, 2023

(65) Prior Publication Data

US 2023/0240517 A1    Aug. 3, 2023

Related U.S. Application Data

(63) Continuation of application No. 16/351,909, filed on Mar. 13, 2019, now Pat. No. 11,589,736.
(Continued)

(51) Int. Cl.
*A61B 1/00* (2006.01)
*A61B 1/005* (2006.01)
(Continued)

(52) U.S. Cl.
CPC ...... *A61B 1/00183* (2013.01); *A61B 1/00042* (2022.02); *A61B 1/00135* (2013.01); *A61B 1/00177* (2013.01); *A61B 1/0057* (2013.01); *A61B 1/015* (2013.01); *A61B 1/018* (2013.01); *A61B 1/051* (2013.01)

(58) Field of Classification Search
CPC . A61B 1/00183; A61B 1/051; A61B 1/00177; A61B 1/00135; A61B 1/015; A61B 1/018; A61B 1/0057; A61B 2017/0034; A61B 1/0055; A61B 1/00179;
(Continued)

(56) References Cited

U.S. PATENT DOCUMENTS 4,353,358 A * 10/1982 Emerson ............... A61B 1/31
600/146
4,911,148 A * 3/1990 Sosnowski ......... A61B 1/00165
600/164
(Continued)

FOREIGN PATENT DOCUMENTS

CN      104883991      9/2015
CN      101972169      1/2016
(Continued)

*Primary Examiner* — Anh Tuan T Nguyen
*Assistant Examiner* — Shankar Raj Ghimire
(74) *Attorney, Agent, or Firm* — Levine Bagade Han LLP

(57) ABSTRACT

An endoscope used for insertion into a patient's body is disclosed herein. The endoscope can comprise an outer sleeve defining a longitudinal axis. The outer sleeve can comprise a first deflecting segment and a second deflecting segment at a distal portion of the outer sleeve and one or more slots at the distal portion. The endoscope can further comprise an inner sleeve positioned within the outer sleeve and comprising a working channel. The inner sleeve can comprise one or more extending elements at a distal portion of the inner sleeve, the one or more extending elements being coupled to the first deflecting segment of the outer sleeve. The endoscope can further comprise a tool advanceable through the working channel, wherein advancement of the tool transitions the distal portion of the outer sleeve between a straight profile and a deflected profile.

13 Claims, 20 Drawing Sheets

Related U.S. Application Data

(60) Provisional application No. 62/642,394, filed on Mar. 13, 2018.

(51) Int. Cl.
*A61B 1/015* (2006.01)
*A61B 1/018* (2006.01)
*A61B 1/05* (2006.01)

(58) Field of Classification Search
CPC ... A61B 1/05; A61B 1/00042; A61B 1/00066; A61B 1/00105
See application file for complete search history.

(56) References Cited

U.S. PATENT DOCUMENTS

| | | | |
|---|---|---|---|
| 5,063,018 A | | 11/1991 | Fontirroche et al. |
| 5,882,346 A | * | 3/1999 | Pomeranz .......... A61B 18/1492 604/510 |
| 5,993,462 A | * | 11/1999 | Pomeranz .......... A61B 18/1492 606/45 |
| 9,549,662 B2 | * | 1/2017 | Demers ................ A61B 1/0011 |
| 10,433,717 B1 | * | 10/2019 | Truckai ............... A61B 1/00094 |
| 11,369,253 B2 | * | 6/2022 | Truckai ................ A61B 1/0008 |
| 11,589,736 B2 | * | 2/2023 | Truckai .............. A61B 1/00183 |
| 11,596,298 B2 | * | 3/2023 | Toth ................... G02B 23/2476 |
| 2003/0181823 A1 | * | 9/2003 | Gatto .................... A61B 1/3132 600/564 |
| 2003/0208192 A1 | * | 11/2003 | Truckai ............. A61B 17/12022 606/41 |
| 2003/0212427 A1 | * | 11/2003 | Truckai ............. A61B 17/12045 606/195 |
| 2004/0092794 A1 | | 5/2004 | Chin et al. |
| 2004/0247849 A1 | * | 12/2004 | Truckai ............. A61B 17/12022 428/292.1 |
| 2009/0149878 A1 | | 6/2009 | Truckai et al. |
| 2010/0211076 A1 | * | 8/2010 | Germain ............ A61B 18/1492 606/84 |
| 2011/0004157 A1 | | 1/2011 | Dewaele et al. |
| 2011/0251615 A1 | * | 10/2011 | Truckai ............... A61B 17/1633 606/191 |
| 2011/0295262 A1 | * | 12/2011 | Germain ............ A61B 17/1642 606/84 |
| 2013/0102846 A1 | * | 4/2013 | Sjostrom .................. A61B 1/07 600/110 |
| 2013/0172676 A1 | | 7/2013 | Levy et al. |
| 2013/0190562 A1 | | 7/2013 | Smith et al. |
| 2014/0046305 A1 | | 2/2014 | Castro et al. |
| 2014/0303611 A1 | * | 10/2014 | Shadduck ............ A61B 18/148 606/33 |
| 2015/0066033 A1 | * | 3/2015 | Jorgensen ............... A61B 34/71 606/170 |
| 2016/0022470 A1 | * | 1/2016 | Gillis ........................ A61F 5/56 128/848 |
| 2016/0346037 A1 | * | 12/2016 | Truckai ................ A61B 18/148 |
| 2017/0035277 A1 | * | 2/2017 | Kucharski ................ A61B 1/05 |
| 2017/0042411 A1 | * | 2/2017 | Kang ........................ A61B 1/31 |
| 2017/0319047 A1 | * | 11/2017 | Poulsen ............... A61B 1/0008 |
| 2018/0049919 A1 | * | 2/2018 | Auld .................... A61B 1/0052 |
| 2018/0084971 A1 | * | 3/2018 | Truckai ............... A61B 1/00082 |
| 2018/0125339 A1 | * | 5/2018 | Gerbo .................... A61B 1/005 |
| 2018/0338672 A1 | * | 11/2018 | Krimsky ............ A61B 1/00121 |
| 2019/0099062 A1 | * | 4/2019 | Ishihara .................. A61B 1/00 |
| 2019/0282073 A1 | * | 9/2019 | Truckai ................... A61B 1/303 |
| 2019/0343370 A1 | * | 11/2019 | Kumagai ............. A61B 1/0052 |

FOREIGN PATENT DOCUMENTS

| | | |
|---|---|---|
| WO | WO 2017/216835 | 12/2017 |
| WO | WO 2019/178180 | 9/2019 |

* cited by examiner

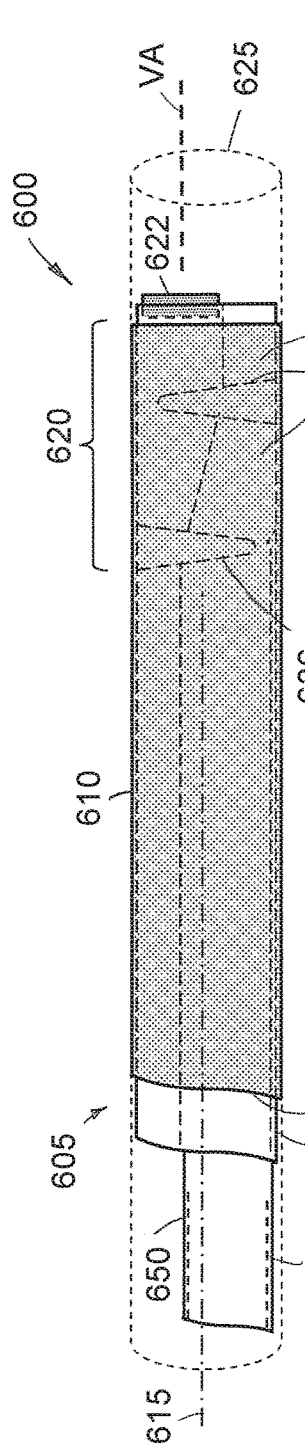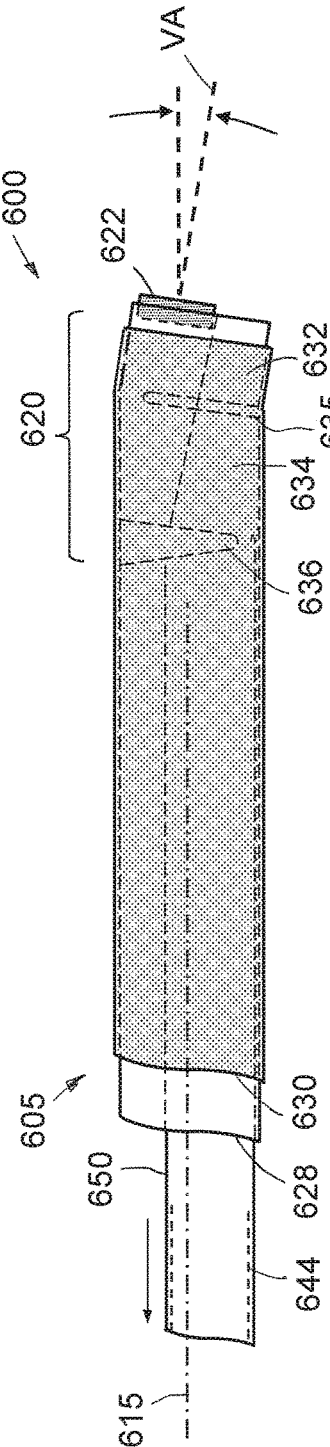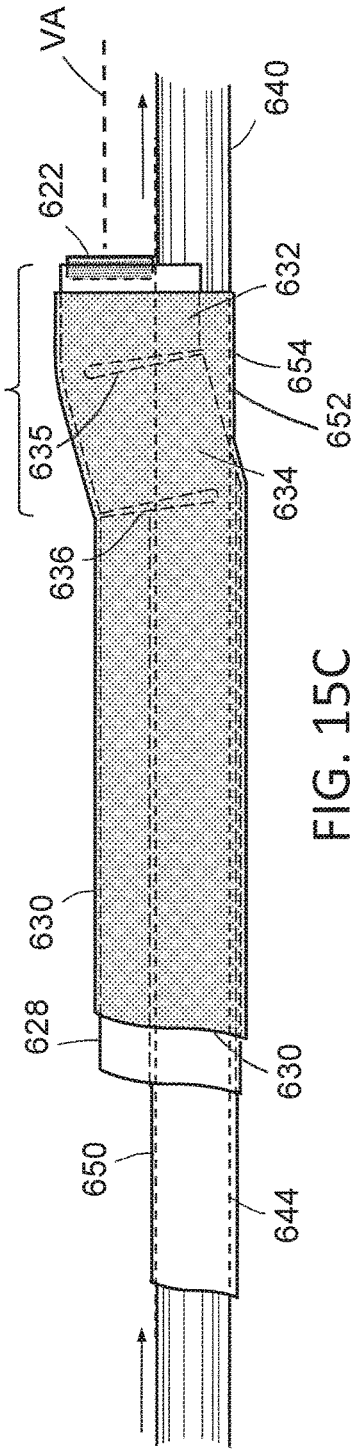

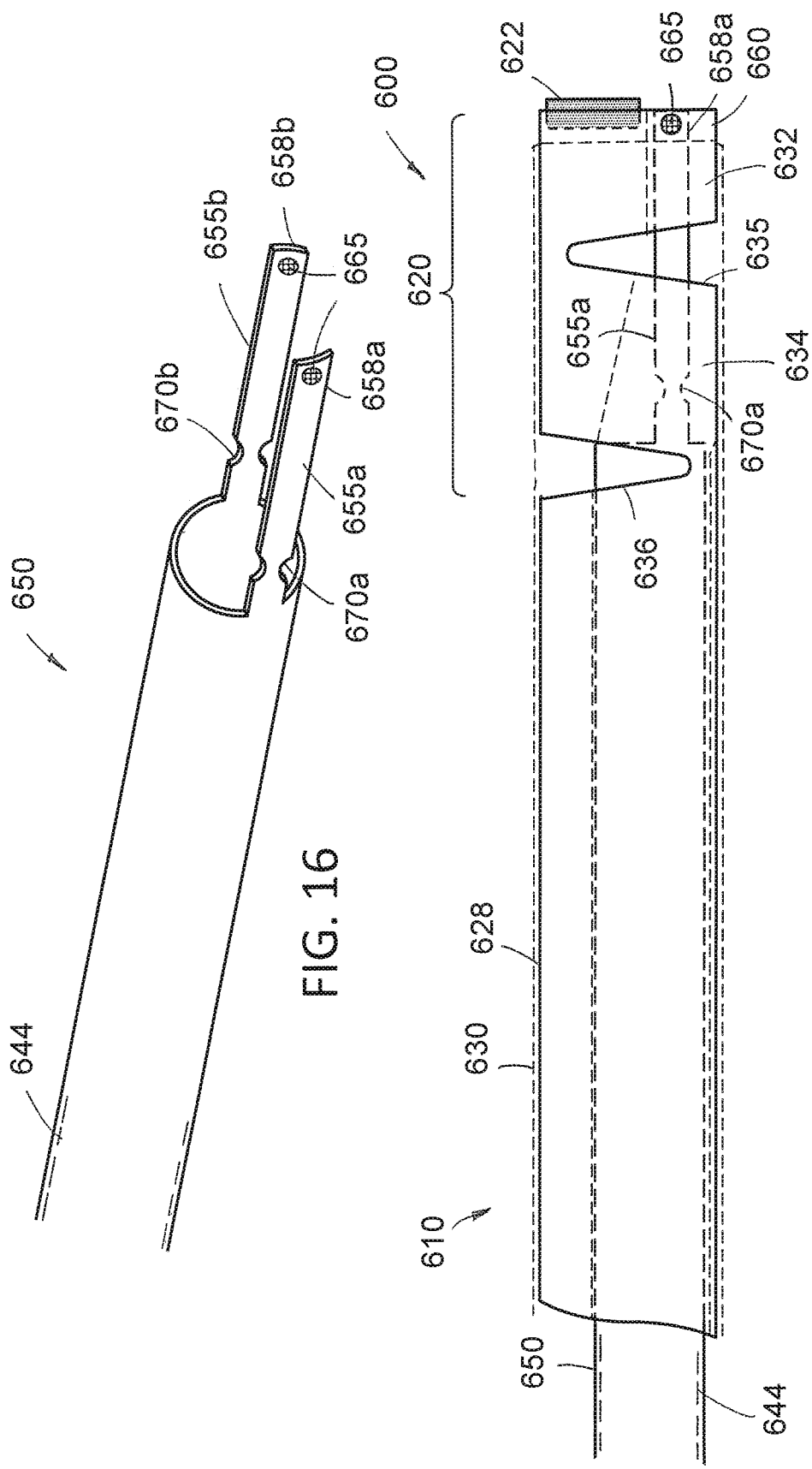

DEFLECTABLE ENDOSCOPE AND METHOD OF USE

CROSS-REFERENCE TO RELATED APPLICATIONS

The present application is a continuation of U.S. patent application Ser. No. 16/351,909 filed Mar. 13, 2019, which claims benefit of priority to U.S. Provisional Application No. 62/642,394 filed on Mar. 13, 2018. This application is also related to PCT/US2019/021977 filed on Mar. 13, 2019. The entirety of each of which are incorporated by reference.

BACKGROUND OF THE INVENTION

Field of the Invention

The present invention relates to an integrated hysteroscopic treatment system which includes an endoscopic viewing system, a fluid management system, a resecting device and a controller for operating all the systems.

SUMMARY OF THE INVENTION

The present disclosure relates to methods, devices and systems related to endoscopic devices and/or procedures. For example, a variation of the device can include an endoscope having an elongated shaft with an image sensor located at a distal end of the elongated shaft, the elongated shaft having a straight cylindrical insertion profile and at least one of deflected profile for orienting the image sensor for peripheral viewing, wherein the image sensor has a diagonal dimension that is at least 50% of a diameter of the distal end of the elongated shaft in the insertion profile; and a working channel in the elongated shaft adapted to accommodate an elongated straight tool extending therethrough when the elongated shaft is in the deflected profile, wherein the diameter of the working channel is at least 50% of the diameter of the distal end of the elongated shaft in the insertion profile.

A variation of the endoscope can include an image sensor that, when in the insertion profile, has a 0 to 15 degree viewing angle relative to a central axis of the insertion profile. In another variation, the image sensor, when in a first deflected profile, has a viewing angle adapted for peripheral viewing. Additional variations include image sensors in the first deflected profile with a 5 to 90 degree viewing angle relative to said central axis.

Variations of the device can include an endoscope wherein the image sensor in a second deflected profile is moved radially outward relative to said central axis. For example, in the second deflected profile the image sensor has a 0 to 15 degree viewing angle relative to said central axis.

Additional variations of the endoscope include a working channel that is configured with a distal section that changes shape between the insertion profile and a deflected profile.

The distal section of the working channel can comprise an elastomeric wall. In additional variations, the elongated shaft has a distal articulating portion for providing the at least one deflected profile. In one example, the distal articulating portion comprises a slotted sleeve.

In additional variations, the endoscope can include an actuator sleeve that is axially moveable relative to the slotted sleeve for moving the articulating portion between the insertion profile and at least one deflected profile. The endoscope can also further include a pull-wire coupled to the slotted sleeve for moving the articulating portion between the insertion profile and at least one deflected profile.

Variations of the device can further include a fluid inflow source communicating with the working channel. The endoscope can also have a negative pressure source communicating with a flow channel extending through the elongated shaft.

In an additional variation, an endoscope for insertion into a patient's body can include an elongated shaft extending about a central axis to a distal end carrying an image sensor having a viewing angle; wherein the shaft has a first non-articulated configuration wherein an image sensor viewing angle is aligned with the central axis for introducing into the patient's body and a second articulated configuration wherein the image sensor viewing angle is angled away from said central axis for peripheral viewing; and a working channel in the shaft adapted to accommodate a rigid straight tool wherein the diameter of the working channel is at least 50% of the shaft diameter in the first non-articulated configuration.

Variations of the endoscope can include a working channel that is configured with a distal portion that changes in cross-sectional dimension between the first non-articulated configuration and the third articulated configuration. As noted herein, the working channel can be configured with a distal portion having an elastomeric wall.

In an additional variation, the present disclosure includes an endoscope, comprising: an elongated shaft extending about a central axis to an articulating distal portion carrying an image sensor having a viewing angle, wherein the shaft is capable of a straight insertion profile and a plurality of articulated profiles; an articulation mechanism configured to have an insertion profile, an articulated profile, and an articulated profile with the image sensor in a radially offset position wherein in the insertion profile the image sensor is in a first radial position allowing a 0 degree viewing angle; in the articulated profile, the image sensor provides a 5 to 90 degree viewing angle; and in the articulated profile with the image sensor in the radially offset position, second radial position the image sensor provides a 0 to 15 degree viewing angle.

The endoscopes described herein can include one or more working channels that extend through the elongated shaft.

The working channel can be configured with a distal portion that changes in cross-sectional dimension between the insertion profile and an articulated profile. As noted above, the working channel can be configured with a distal portion having an elastomeric wall.

Additional advantages of the invention will be apparent from the following description, the accompanying drawings and the appended claims.

BRIEF DESCRIPTION OF THE DRAWINGS

Additional aspects of the invention will become clear from the following description of illustrative embodiments and from the attached drawings, in which:

FIG. 15A is an elevational view of the distal working end of the variation of a single-use endoscope that has an articulating section for adjusting the viewing angle of the imaging sensor, with the endoscope shaft assembly in a straight non-articulated configuration for insertion into a patient's body with the image sensor aligned with the central axis of the endoscope shaft.

FIG. 15B is a view of the working end of the endoscope of FIG. 15A in an articulated configuration with the image sensor angled away from the central axis of the endoscope shaft assembly for peripheral viewing.

FIG. 15C is another view of the working end of the endoscope of FIGS. 15A-15B in another articulated configuration wherein the image sensor is offset from the central axis of the endoscope shaft in is a viewing angle that is aligned with the central axis.

FIG. 16 is a perspective view of an axially-movable actuator sleeve that is adapted for articulating the working end of the endoscope of FIGS. 15A-15C.

FIG. 17A is a cut-away view of the working end of the endoscope corresponding to FIG. 16A showing the outline of the actuator sleeve of FIG. 16 in the shaft assembly.

DETAILED DESCRIPTION OF THE INVENTION

Figure 1A:
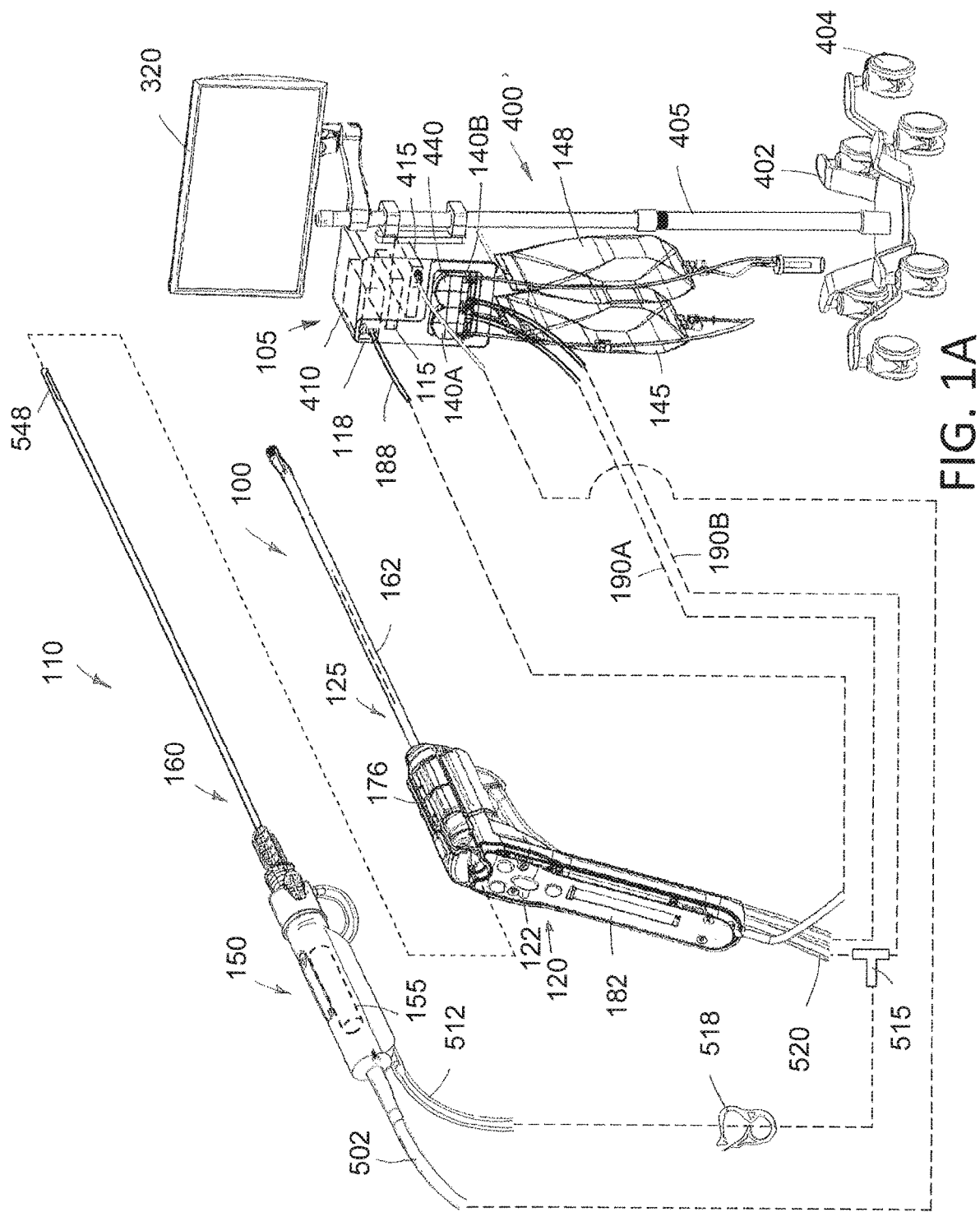
FIG. 1A is a perspective view of components of a hysteroscopic treatment system corresponding to the invention, including an endoscopic viewing system, a fluid management system and a resecting device.

FIG. 1A illustrates a hysteroscopic treatment system 50 corresponding to the invention which comprises multiple components including an endoscopic viewing system 100, a fluid management system 105 and a resection device 110 that are all operated by a controller 115 in a base unit 118 with integrated software algorithms configured to operate all the systems and subsystems.

More in particular, the endoscopic viewing system 100 of FIGS. 1A, 1B, 2A and 2B includes a re-usable handle component 120 with a finger-actuated control pad 122 and a disposable endoscope component 125 that carries a distal electronic imaging sensor 128. The fluid management system 105 includes a first peristaltic inflow pump 140A and second peristaltic outflow pump 140B, a fluid source 145 and fluid collection reservoir 148 together with a fluid weight measurement subsystem. The resection device 110 includes a re-usable handpiece 150 with a motor drive 155 and a disposable cutting component 160 for resecting tissue in a hysteroscopic procedure, for example, used for resecting uterine polyps. Each of the systems and subsystems will be described in more detail below.

Endoscopic Viewing System

Figure 1B:
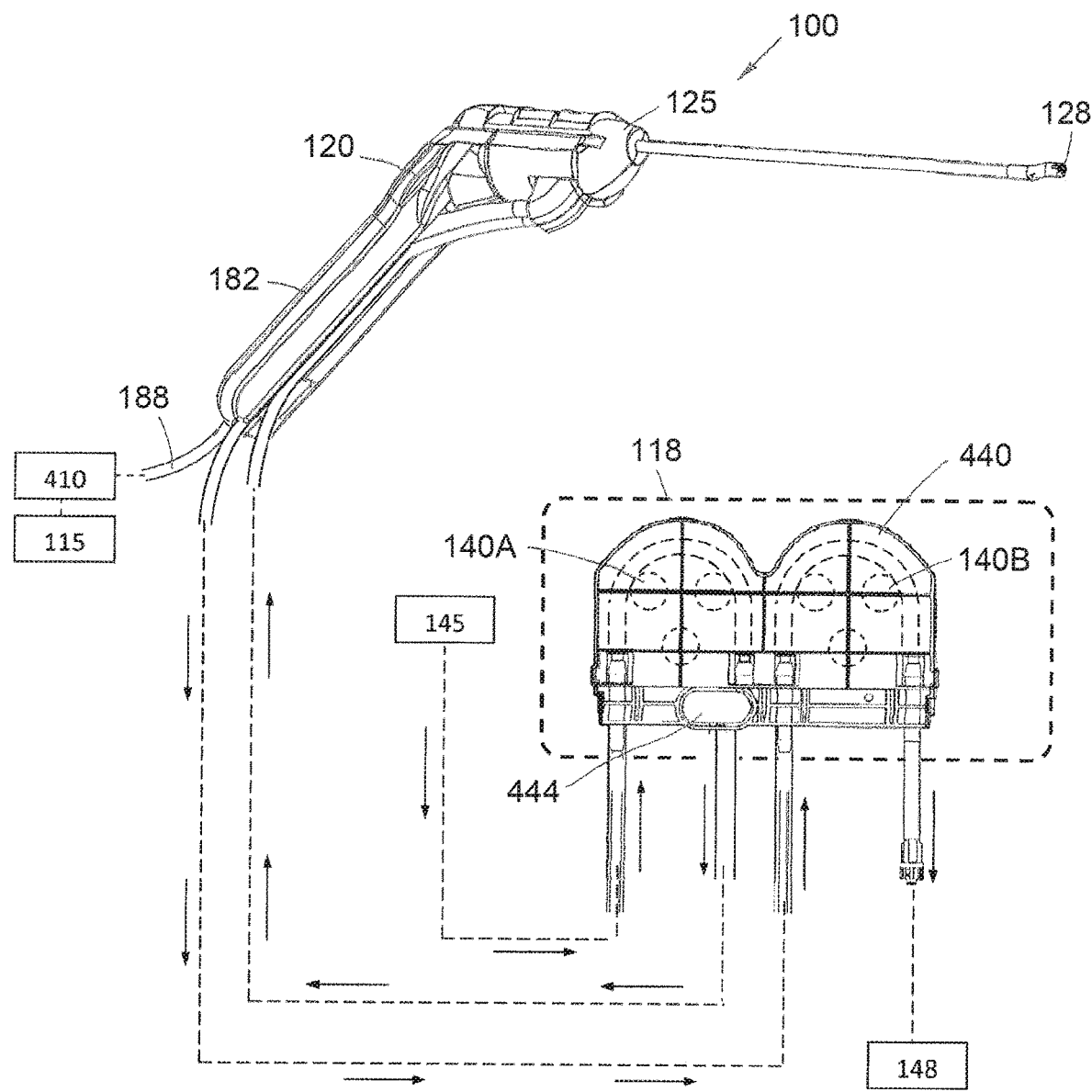
FIG. 1B is a perspective view of the endoscopic viewing system and a schematic view of the fluid management system of FIG. 1A.
Figure 2A:
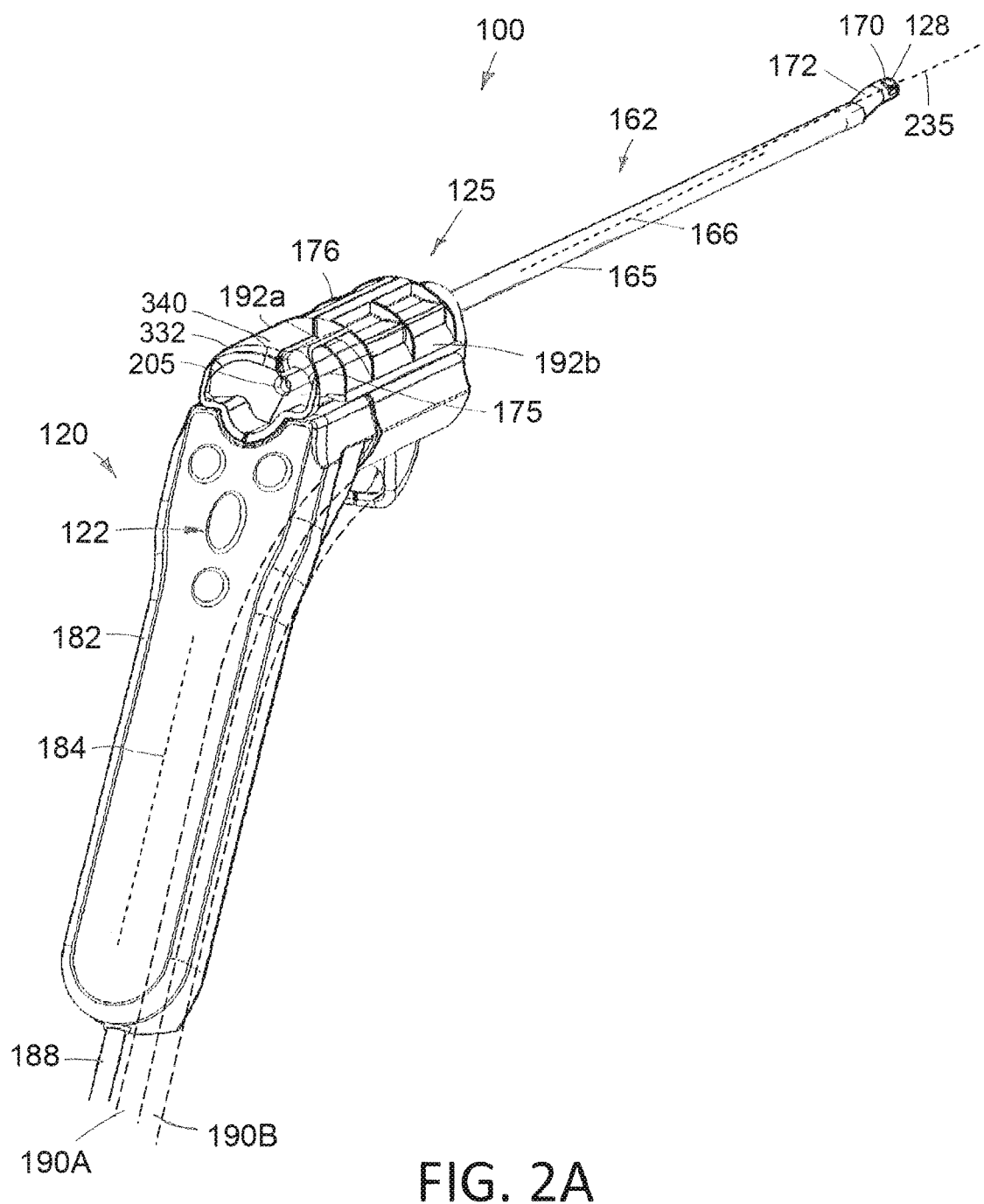
FIG. 2A is a perspective view of the endoscopic viewing system of FIG. 1B from a different angle.
Figure 2B:
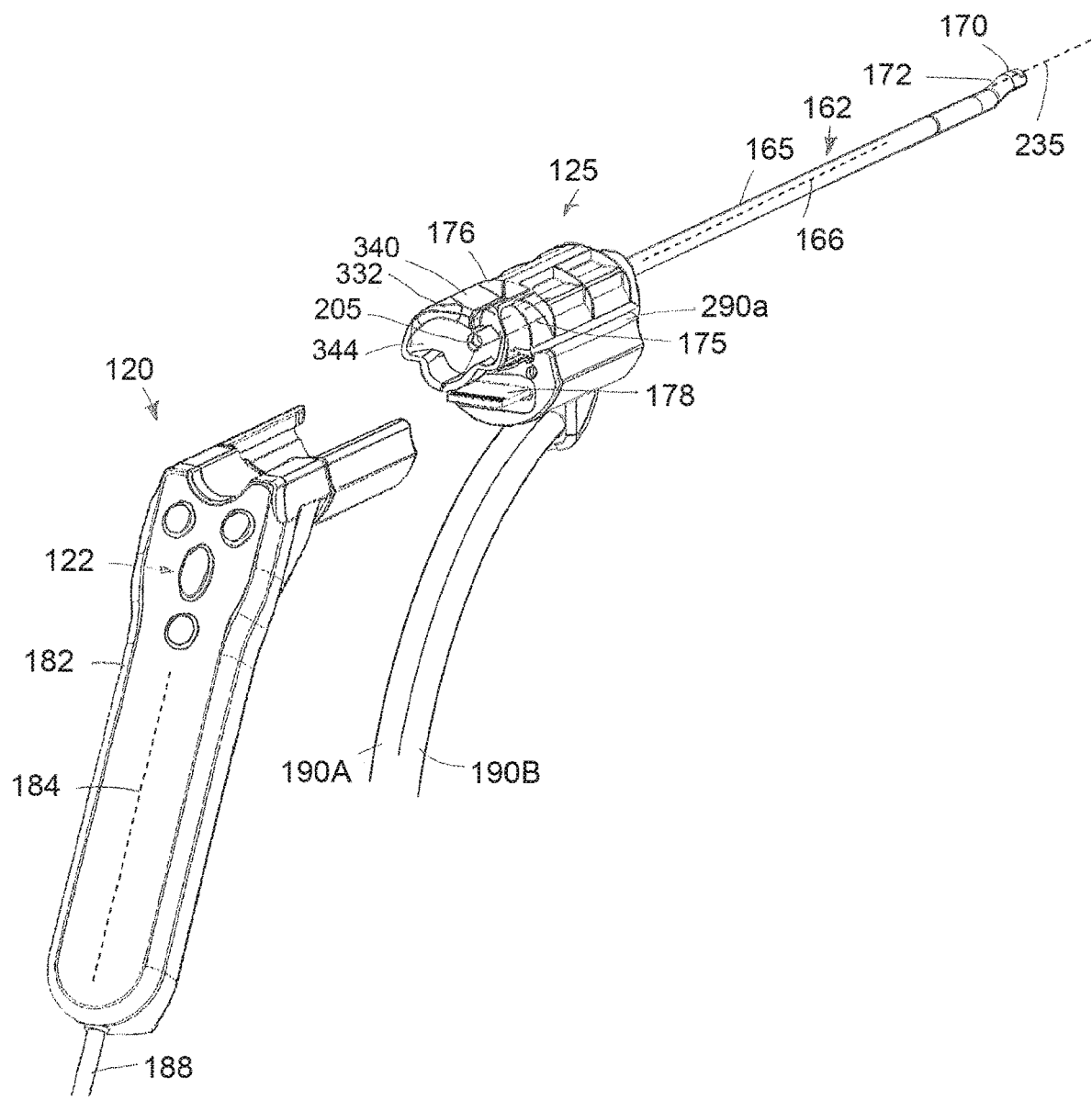
FIG. 2B is a perspective view of the endoscopic viewing system of FIG. 2A showing a single-use disposable endoscope component separated from a re-usable handle component.

Referring to FIGS. 1B, 2A and 2B, it can be seen that the endoscopic viewing system 100 includes a handle component 120 and a detachable single-use endoscope component 125. The endoscope shaft assembly 162 has a straight proximal portion 165 that extends about a central longitudinal axis 166. The shaft includes a distal tip section 170 that is offset from the longitudinal axis 166. A shaft transition section 172 extends at an angle between the straight proximal shaft portion 165 and the offset distal tip section 170. The imaging sensor 128 is disposed at the distal end of the offset tip section 170. As can be seen in FIGS. 2A-2B, the endoscope component 125 has a working channel 175 extending therethrough which will be described in more detail below. In one variation, endoscope shaft assembly 162 has a diameter ranging between 4 mm and 10 mm with an overall length configured for use in hysteroscopy. More commonly, the shaft diameter is from 5 mm to 6 mm in diameter.

In one variation, the endoscope component 125 has a hub 176 that is adapted for sliding, detachable engagement with the handle component 120 as can be best seen in FIG. 2B. The endoscope shaft assembly 162 extends distally from the hub 176 and the angled transition section 172 and distal tip section 170 are oriented in a superior or upward direction relative to the hub 176. As can be seen in FIG. 2B, the hub 176 carries a projecting electrical connector 178 that is adapted to couple to a mating electrical connector 180 in the handle component 120 that can be best seen in FIG. 3. In some variations, the endoscope shaft assembly 162 may be rotated relative to the hub 176 (not shown in FIGS. 2A-2B). While FIGS. 2A-2B illustrates that the endoscope component 125 is configured for axial sliding engagement with the handle component 120, it should be appreciated that the angled pistol grip portion 182 of the handle component 120 could plug into the endoscope component 125 in a different arrangement, such as a male-female threaded connector aligned with the axis 184 of the angled grip portion 182. As will be described below, the endoscope component 125 comprises a sterile device for use in the sterile field, while the handle component 120 may not be sterilized and is typically adapted for use for use in a non-sterile field. A cable 188 extends from the handle to an imaging processor 410, controller 115 and power source described further below (FIGS. 1A-1B).

Figure 9A:
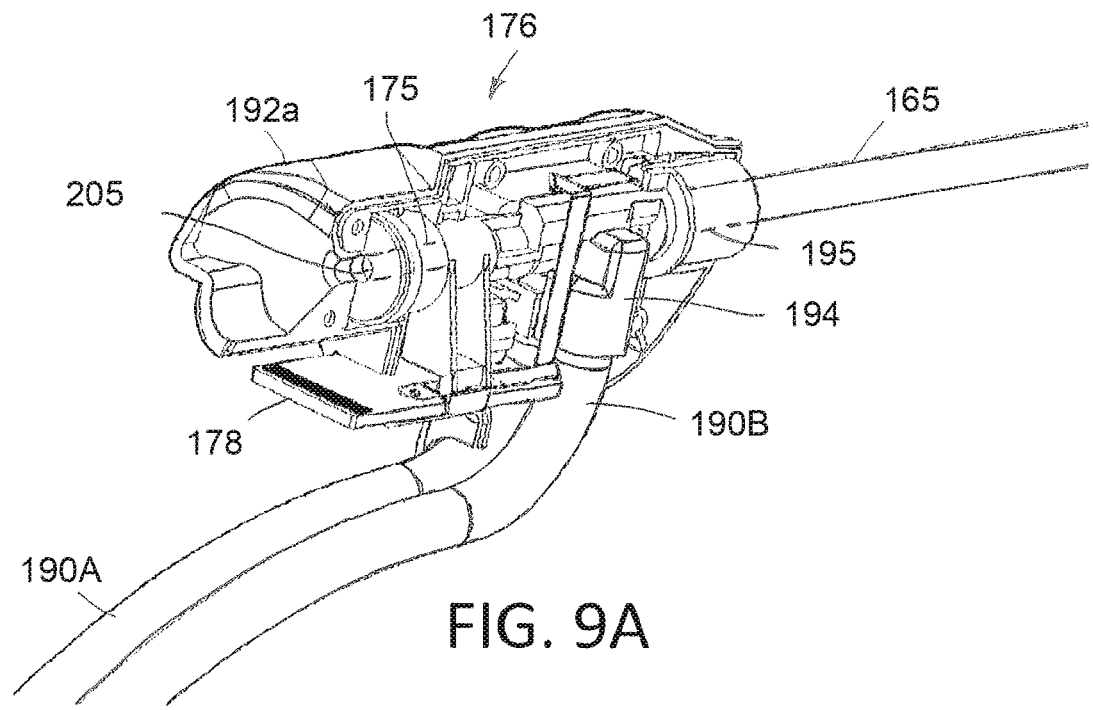
FIG. 9A is another perspective view of a partially disassembled endoscope component of the system of FIGS. 1A-2B showing inflow and outflow channels in a channel housing and a flex circuit coupled to the image sensor and the pressure sensor.
Figure 9B:
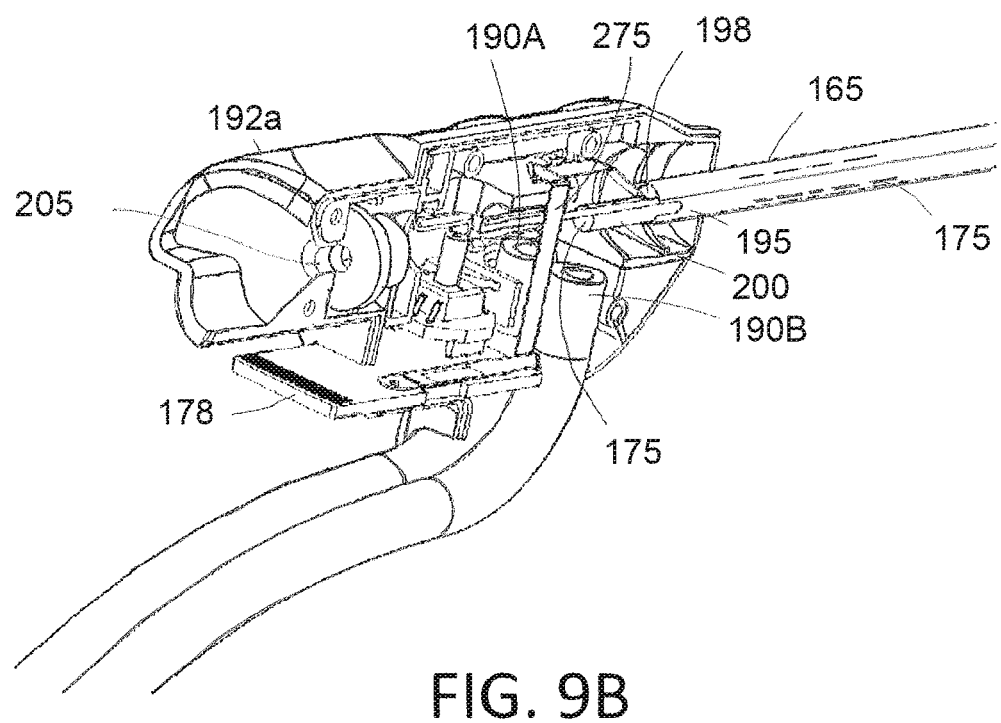
FIG. 9B is a perspective view similar to that of FIG. 9A with the channel housing removed to show the inflow and outflow channels in the shaft assembly.

As can be seen in FIGS. 1A, 1B and 2B, the endoscope component 125 includes fluid inflow tubing 190A and fluid outflow tubing 190B that communicate with the fluid management system 105 which is further described below and shown generally in FIGS. 1A-1B. As can be understood from FIGS. 2B and 9A, the endoscope hub 176 can consist of two injection-molded plastic shell elements 192a and 192b, and FIG. 9A shows one side element removed to the interior of the hub 176. It can be seen that both the inflow tubing 190A and outflow tubing 190B are coupled to an injection-molded flow channel housing 194 in the hub 176 that is fixed to the proximal end 195 of the endoscope shaft assembly 162. FIG. 9B is a cut-away view similar to that of FIG. 9A with the housing 194 removed to show that inflow tubing 190A communicates with an open space or flow channel 198 extending through the endoscope shaft assembly 162 that is outward from the thin-wall sleeve 200 that defines the working channel 175 therein. The flow channel 198 can also be seen in FIGS. 6A-6B at its distal termination 202 in the endoscope shaft assembly 162. As can be understood from FIG. 9B, the outflow tubing 190B communicates with a proximal end 204 of sleeve 200 and working channel 175 which also can be seen in FIGS. 6A-6B. In a method of use that will be described below, the endoscope shaft assembly 162 can be navigated through a patient's endocervical canal with the inflow and outflow pumps 140A and 140B (see FIGS. 1A-1B) operating to provide continuous irrigation to the distal tip of the endoscope component 125 together with endoscopic viewing by means of the image sensor 128. Such a variation will thus allow fluid inflows through channel 198 and fluid outflows through the working channel 175.

Now turning to FIGS. 6A-6B, the endoscope shaft assembly 162 has a small insertion profile or configuration that consists of the outer diameter of the shaft assembly which includes the proximal straight section 165, the angled section 172 that is relatively short as will be described further below and the distal section 170 (see FIG. 6A). Of particular interest, referring to FIG. 6B, the distal portion of the endoscope shaft assembly 162 includes a working channel portion 175' that is reconfigurable between a first smaller cross-section as shown in FIG. 6A for accommodating fluid outflows and a second larger cross-section as shown in FIG. 6B for accommodating a shaft of the resecting device 110 (FIG. 1A) or another similar tool shaft.

Figure 6A:
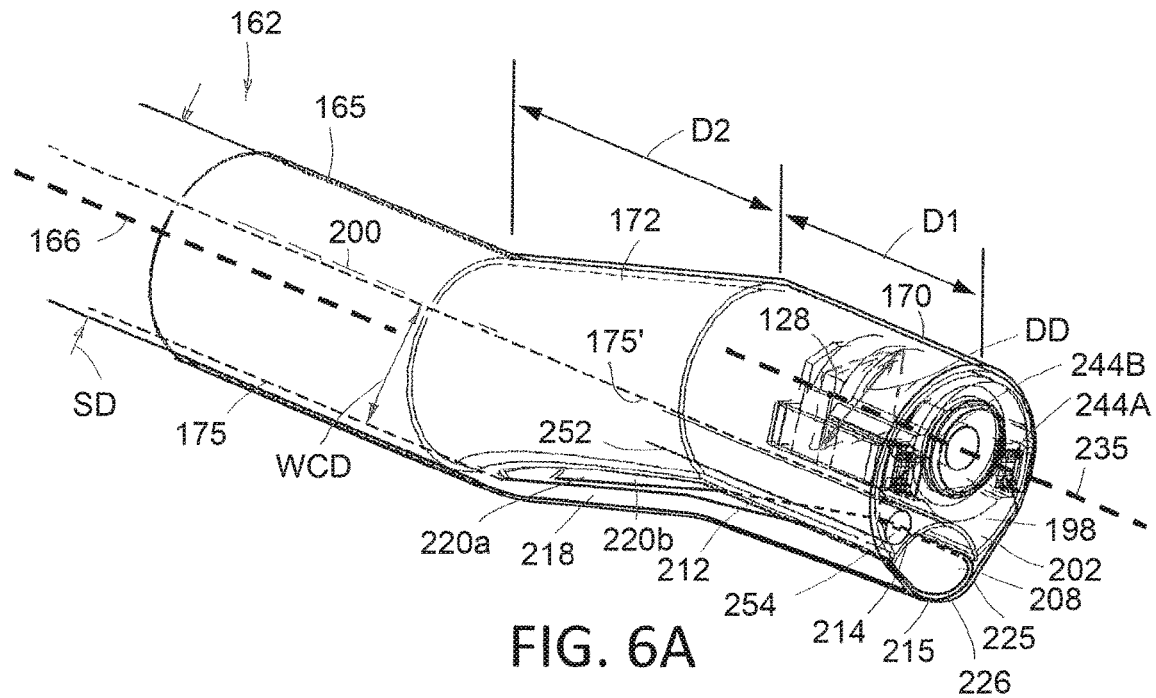
FIG. 6A is an enlarged perspective view of the distal end of the endoscope shaft assembly showing a working channel with a distal channel portion in a reduced cross-sectional configuration for introduction into a patient's body.
Figure 6B:
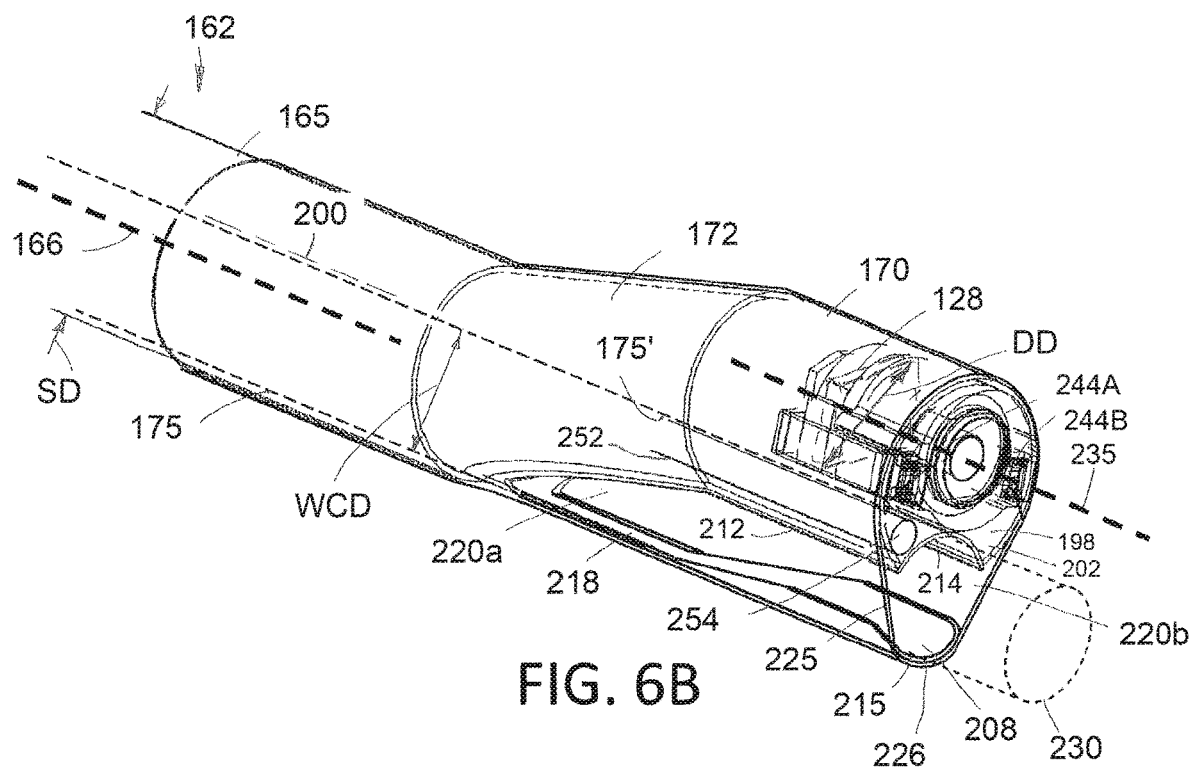
FIG. 6B is another view of the distal end of the endoscope shaft assembly of FIG. 6A showing the distal working channel portion in an expanded cross-sectional configuration when a tool shaft is introduced though the working channel.

In one variation shown in FIGS. 2B and 6B, it can be seen that the sleeve 200 that defines the working channel 175 extends in a straight configuration through the endoscope component 125 from its proximal end 205 to its open distal termination 208. As can be seen in FIGS. 6A and 6B, the distal end 212 of sleeve 200 has a superior surface 214 that is straight and rigid. The working channel sleeve 200 has an inferior or lower sleeve portion 215 that is flexible and in one variation has a living hinge portion 218 below sidewall cut-outs 220a and 220b in the sleeve 200. Further, the distal end of the endoscope component 125 includes an elastomeric sleeve 225 that surrounds the angled shaft portion 172 and the distal shaft section 170 as well as a distal portion of the proximal straight shaft 165. Thus, as can be seen in FIG. 6A, the elastomeric sleeve 225 has sufficient elastic strength to collapse or constrict the working channel portion 175' to the smaller cross-section as seen in FIG. 6A.

As can be seen in FIG. 6A, the lower sleeve portion 215 includes a sleeve wall 226 with sufficient curvature to maintain an open pathway through the working channel 175 when the elastomeric sleeve 225 constricts the working channel portion 175' which thereby always provides an open fluid outflow pathway. For example, the sleeve wall 226 can have the diameter as a proximal portion of sleeve 200 and extend over a radial angle ranging from 30° to 90°. While the lower sleeve portion 215 shown in FIG. 6A comprises a portion of the wall of metal sleeve 200, in another variation, the flexible lower sleeve portion 215 may be any bendable plastic material or a combination of plastic and metal.

FIG. 6B next shows the working channel portion 175' in its second expanded configuration as when a physician inserts an elongated tool shaft 230 (phantom view) through the working channel 175. Such a tool shaft 230 will initially slide along the hinge portion 218 of the lower sleeve portion 215 and then stretch the elastomeric sleeve 225 to open distal working channel portion 175' to allow the tool shaft 230 to extend through the working channel. In other words, the elastomeric sleeve 225 will be stretched or deformed to a tensioned position as shown in FIG. 6B as a tool shaft 230 is inserted through the distal working channel portion 175'. When the tool shaft 230 is withdrawn from the working channel portion 175', the elastomeric sleeve 225 will return from the tensioned position of FIG. 6B to the repose or non-tensioned position of FIG. 6A to return the working channel portion 175' to the constricted configuration FIG. 6A.

In general, the endoscope component 125 corresponding to the invention allows for the use of an image sensor 128 having a large diagonal dimension relative to the insertion profile or diameter of the endoscope shaft assembly 162 while at the same time providing a working channel 175 that has a large working channel diameter WCD relative to the insertion profile or diameter of the endoscope shaft assembly 162. More in particular, the endoscope component 125 comprises a shaft assembly 162 having a shaft diameter SD extending to a distal shaft section 170, an image sensor 128 with a diagonal dimension DD carried by the distal shaft section 170 and a working channel 175 having a diameter WCD extending through the shaft assembly 162, wherein the working channel portion 175' in the distal end of the shaft assembly 162 is adjustable in shape to accommodate a tool shaft introduced therethrough and wherein the combination or the sensor's diagonal dimension DD and the working channel diameter WCD is greater than the shaft diameter SD (see FIG. 6B). In a variation, the sensor diagonal dimension DD is greater than 50% of the shaft diameter SD or greater than 60% of the shaft diameter. In a variation, the working channel diameter WCD is greater than 30% of the shaft diameter, greater than 40% of the shaft diameter or greater than 50% of the shaft diameter. In other words, the working channel portion 175' in the distal end is adjustable between a first cross-sectional dimension and a second cross-section dimension. In the variation of FIGS. 6A-6B, the working channel portion 175' in the distal region of the endoscope shaft assembly 162 is adjustable between a partially constricted shape and a non-constricted shape.

In one variation, referring to FIG. 6A, the distal section 170 of the endoscope shaft assembly 162 has an axial dimension D1 ranging from 5 mm to 20 mm. Also referring to FIG. 6A, the angled shaft section 172 extends over a similar axial dimension D2 ranging from 5 mm to 20 mm. Still referring to FIG. 6A, the central axis 235 of distal shaft section 170 can be parallel to and offset from the longitudinal axis 166 of the straight shaft section 165 by a distance ranging from 1 mm to 8 mm.

Figure 7:
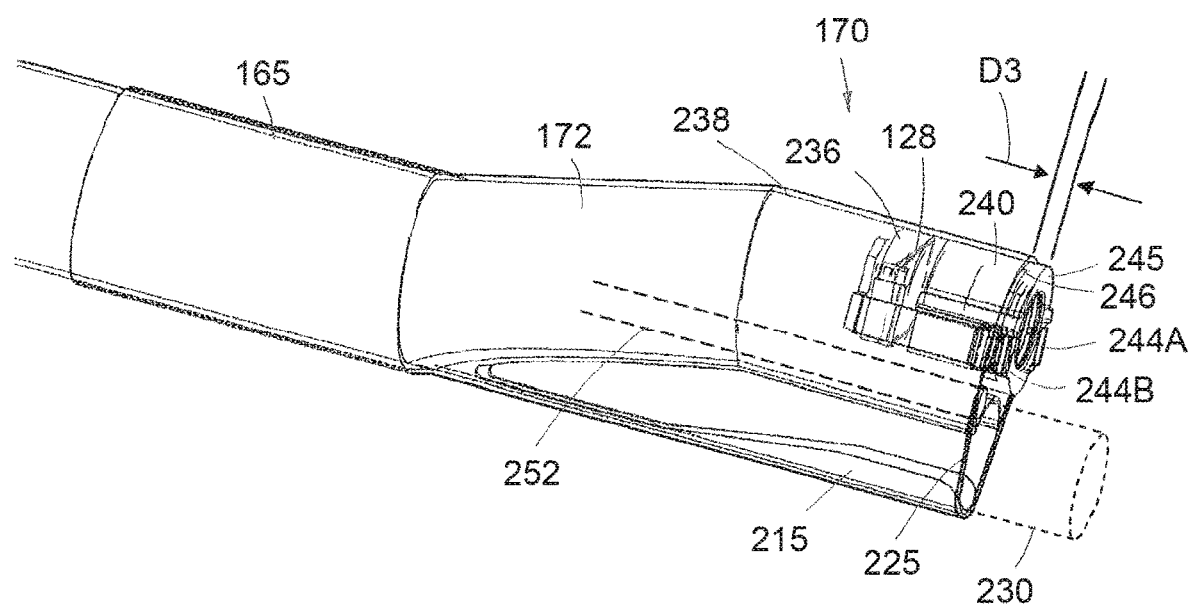
FIG. 7 is another view of the distal end of the endoscope shaft assembly of FIG. 6B showing the distal working channel portion in an expanded cross-sectional sensor and lens stack.

Now turning to FIG. 7, the image sensor 128 is carried in a housing 236 that also carries a lens assembly 240 as is known in the art. The sensor and lens housing 236 is then carried in a thin wall sleeve 238 that comprises the distal endoscope section 170. Further, one or more light emitters, for example, LEDs indicated 244A and 244B carried on either side of the image sensor housing 236. Of particular interest, the distalmost surface 245 of the lens assembly 240 and the LEDs 244A and 244B is disposed distally outward from the distal end 246 of the thin-wall sleeve 238 as shown in FIG. 7. It has been found that providing such a distalmost surface 245 of the lens assembly and the LEDs outwardly from the shaft sleeve 238 improves lighting from the LEDs 244A and 244B as well as improving the field of view of the image sensor 128. The distance indicated at D3 in FIG. 7 can range from 0.2 mm to 2.0 mm.

Figure 8:
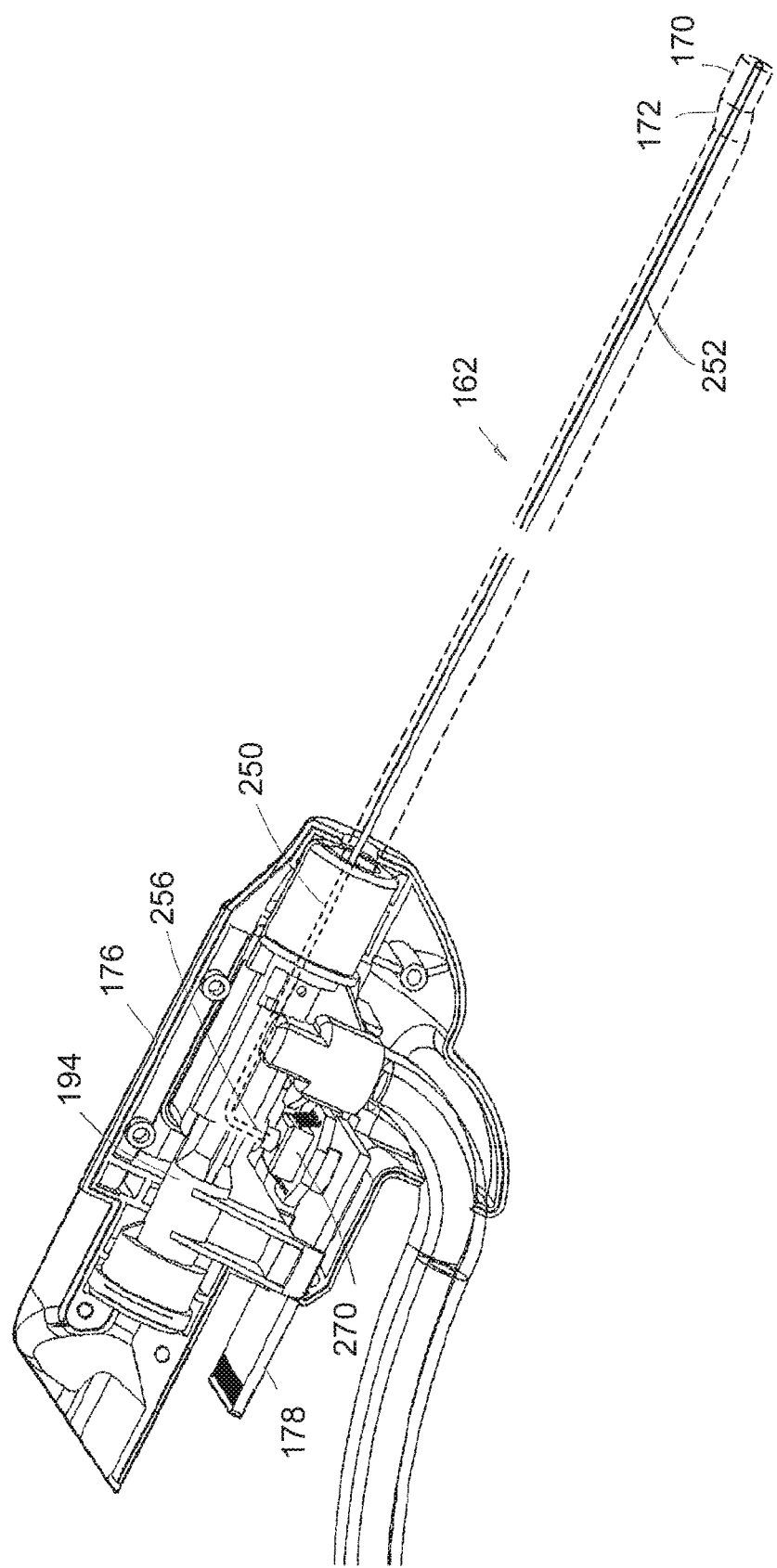
FIG. 8 is a perspective view of a partially disassembled endoscope component of the system of FIGS. 1A-2B showing a dedicated pressure sensing channel and disposable pressure sensor.

Now referring to FIGS. 7 and 8, another aspect of the invention comprises a dedicated fluid pressure sensing channel 250 that extends through a thin wall sleeve 252 in the endoscope shaft assembly 162. As can be seen in FIGS. 6A-6B, the distal end 254 of the pressure sensing sleeve 252 is open in the distal surface of the endoscope component 125. Referring to FIG. 8, the proximal end 256 of the pressure sensing channel 250 extends to the housing 194 in the hub 176 to communicate with a disposable pressure sensor 270. The pressure sensor 270 has electrical leads coupled thereto through the electrical connector 178 in hub 176 to thereby send electrical signals indicating pressure to the controller 115 (FIG. 1A) as will be described further below. Thus, in one aspect, the disposable endoscope component carries a single-use pressure sensor 270 coupled by a detachable connector to a remote controller 115.

In one variation, referring to FIG. 8, the thin wall sleeve 252 consists of a hydrophobic material, which can be any suitable polymer such as PFTE, having an interior diameter ranging from 0.25 mm to 2.5 mm. Often, the inner diameter of the thin wall sleeve 252 is between 0.5 mm and 1.5 mm. It has been found that a hydrophobic surface in the pressure sensing channel 250 will prevent the migration of fluid into the channel and thereby trap an air column in the channel communicating with the pressure sensor 270. The compressibility of the air column in the pressure sensing channel 250 does not significantly affect the sensed pressure since the channel diameter is very small. In another variation, the metal sleeve 252 can be coated with a hydrophobic surface or an ultrahydrophobic surface.

Now turning to FIGS. 6A and 9B, the image sensor 128 and LEDs 244A and 244B are connected to an elongated flex circuit 275 that extends from electrical connector 178 in hub 176 through the endoscope shaft assembly 162. It has been found that only a flex circuit 275 is capable of carrying a sufficient number of electrical leads to the image sensor 128, the LEDs and the pressure sensor 270 to provide for system operation, wherein the number of electrical leads can range from 10 to 100. Further, the flex circuit 275 can extend through the shaft assembly 162 with an interior space that also functions as the fluid flow channel since the flex circuit 275 adequately insulates all the electrical leads.

Handle Component of the Endoscopic Viewing System

Figure 3:
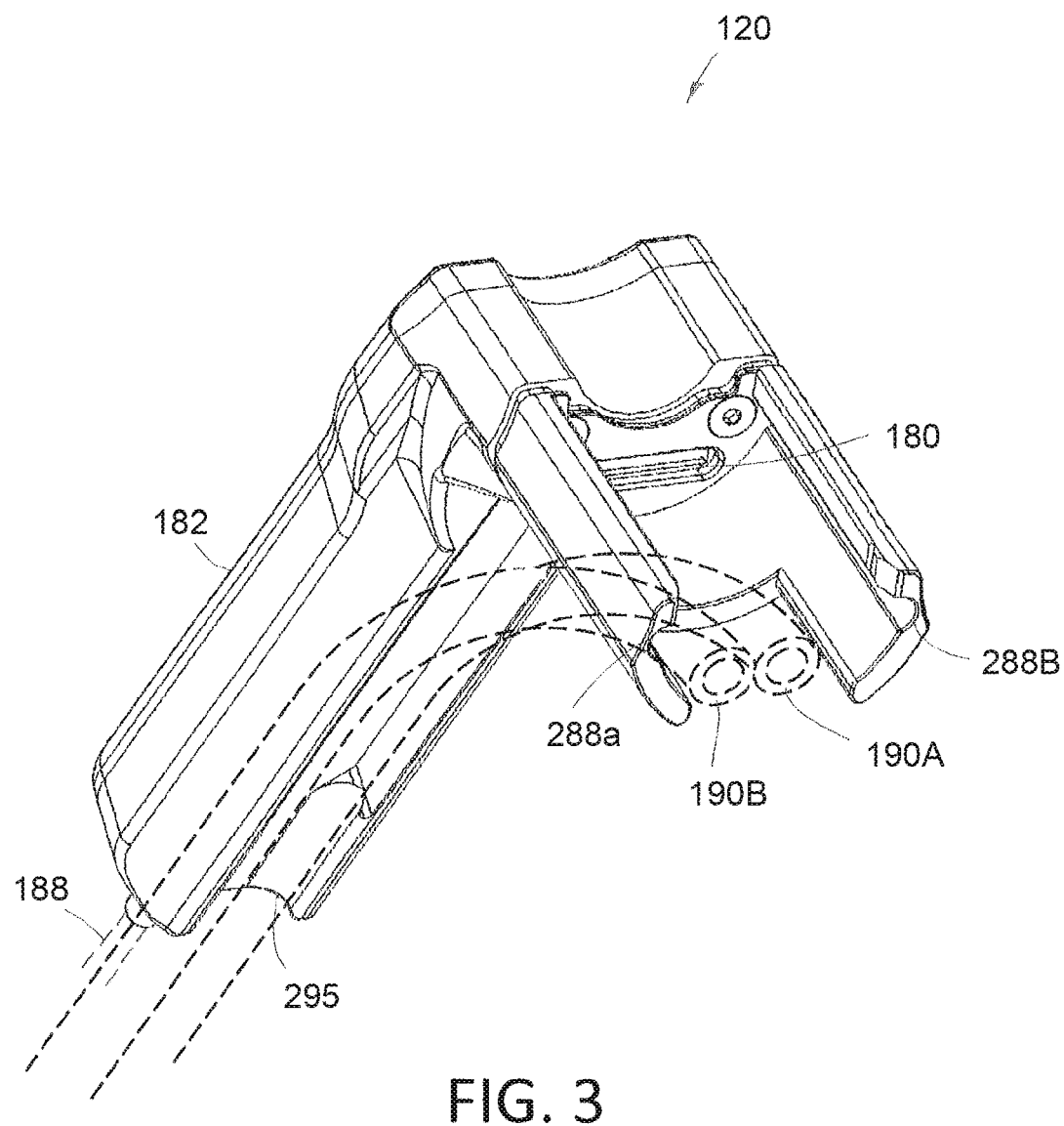
FIG. 3 is a view of a handle component, which shows an electrical connector that interfaces with a projecting electrical connector of a hub of an endoscope component.

Now referring to FIGS. 2B and 3, it can be seen that the handle component 120 has an angled pistol grip portion 182 with an axis 184 that is angled from 10° to 90° away from the longitudinal axis 166 of the endoscope's proximal shaft portion 165. The grip portion 182 includes a control pad 122 that carries actuator buttons for operating all the functions of the treatment system, for example, including (i) operating the fluid management system 105, (ii) capturing images or videos from sensor 128, (iii) adjusting light intensity from the LEDs 244A and 244B, etc. The interior of the handle component 120 also can carry an image processor. or such an image processor may be located in the control unit or base unit 118 shown in FIG. 1A.

FIG. 3 is a view of the handle component 120 from a different angle which shows the electrical connector 180 that interfaces with the projecting electrical connector 178 of the hub 176 of the endoscope component 125. FIG. 3 further shows receiving channels 288a and 288b that receive projecting rail elements 290a and 290b of the endoscope hub 176 as can be seen in FIG. 2B. In FIG. 3, it also can be seen that the grip portion 182 has a recessed channel 295 therein that is adapted to receive and lock in place the inflow and outflow tubing 190A and 190B so as to integrate the tubing set with the pistol grip 182 during use. This feature allows the inflow and outflow tubing to not interfere with operation of the endoscope component 125 or the resecting device 110 introduced through the working channel 175 as will be described in more detail below.

Figure 4:
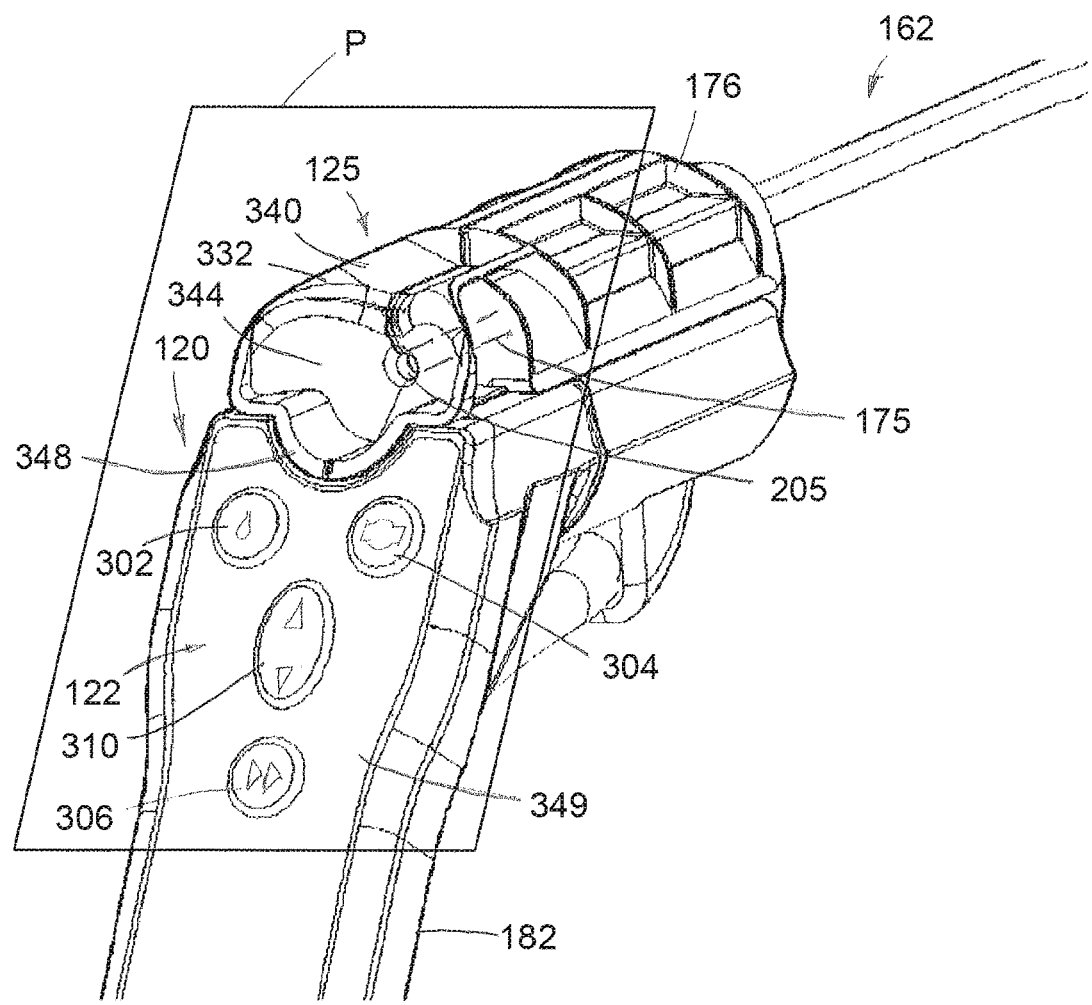
FIG. 4 is a perspective view of the endoscopic viewing system of FIG. 2A showing a finger-actuated control panel.

Now turning to FIG. 4, the enlarged view of the assembled handle component 120 and endoscope component 125 shows the control pad 122 with four actuator buttons or switches which are adapted to operate the system. In one variation, actuator 302 is adapted for turning on and off irrigation, or in other words actuating the fluid management system 105 as will be described further below. Actuator 304 is adapted for image or video capture. In a variation, momentary pressing the actuator 304 will capture a single image and longer pressure on the actuator will operate a video recording.

Actuator or scrolling button 306 has a scrolling function, wherein pressing the scrolling button 306 will cycle through various subsystems that then can be further adjusted by the central button or up/down actuator 310, which is adapted for increasing, decreasing or otherwise changing an operating parameter of any selected subsystem. In one example, the scrolling button 306 can be actuated to cycle through the following subsystems and features: (i) fluid inflow/outflow rate from the fluid management system 105; (ii) the set pressure which is to be maintained by fluid management system 105; (iii) fluid deficit alarm which is calculated by the fluid management system 105; (iv) optional selection of still image capture or video capture, and (v) LED light intensity. Then, the physician can activate the central up/down actuator 310 to adjust an operating parameter of the selected subsystem. As will be described further below, the selection of subsystems as well as the real-time operating parameters of each subsystem will be displayed on a video monitor or display 320 as shown in FIG. 1A. Thus, it can be understood that the physician may operate the scrolling button 306 to scroll through and select any subsystem or feature while observing such as selection on the display 320, and then actuate the up/down actuator 310 can adjust an operating parameter which also can be observed on the display 320.

In another aspect of the invention, the controller 115 includes a control algorithm for operating the control pad 122 which provides a jump back to a default condition after the scroll button or actuator 306 has been used by the physician. For example, there is a default condition in which a selected subsystem is actuatable by the central up/down actuator 310. In one variation, the default subsystem is the fluid inflow/outflow rate, which may be the most commonly used subsystems that will be actuated by the physician to control fluid flow into and out of the working space. Thereafter, as described above, the physician may use the scrolling button 306 to select another subsystem for adjustment of an operating parameter. If, however, the physician does not continue to scroll between the various subsystems for a predetermined amount of time, then the control algorithm will jump back to the default subsystem, which may be the fluid inflow/outflow rate. The predetermined amount of time, or timeout, with the control algorithm to jump back to the default condition may be anywhere from 1 second to 10 seconds, more often between 2 seconds and 5 seconds.

Figure 5:
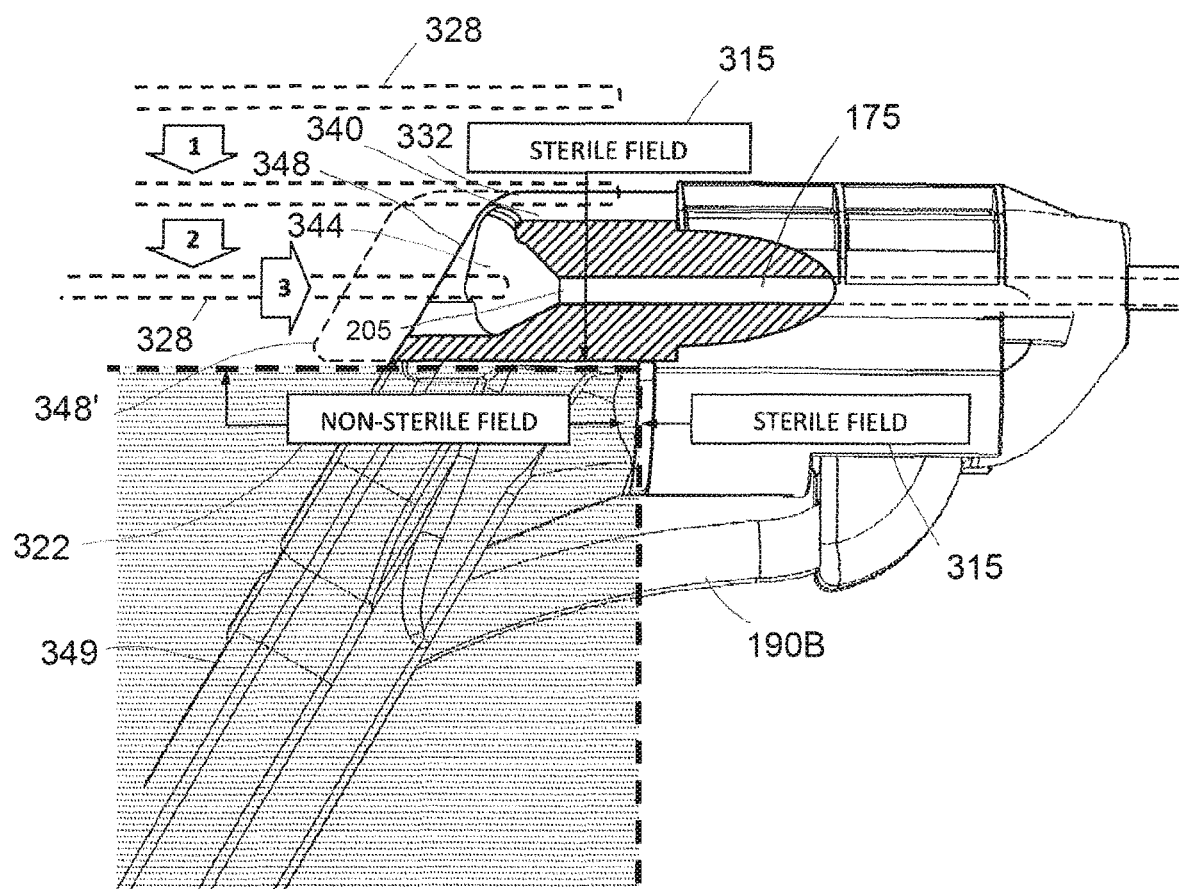
FIG. 5 is a cut-away side view of the endoscopic viewing system of FIG. 2A showing a sterile and non-sterile fields of the components.

Now turning to FIG. 5, a schematic side view of the assembly of the handle component 120 with endoscope component 125 as shown to illustrate the sterile field 315 and the non-sterile field 320 relative to the endoscope assembly. As can be understood, the disposable endoscope component 125 is sterilized and the physician or nurse would remove the component 125 from sterile packaging which would then define a sterile field 315. The endoscope component 125 then would be mated with the handle component 120 which defines the non-sterile field 320. In other variations (not shown), a plastic film or other plastic housing with the beast zero could cover the handle portion 120. FIG. 5 further illustrates a method that would be employed by the physician to insert an elongated tool shaft 328 into the working channel 175 in a manner that would ensure the sterility of the tool shaft 328. As can be seen in FIGS. 2A, 2B, 4 and 5, the superior surface 332 of the hub 176 includes a trough or recessed saddle 340 in which the physician can initiate contact with the tool shaft 328 which is indicated by an arrow in FIG. 5 and is numbered as step 1. Thereafter, as indicated by an arrow as step 2, the tool shaft 328 can be guided downward from the saddle 340 into the cone-shaped recess 344 in hub 176 which tapers distally to transition into the open proximal end 205 of the working channel 175. Thereafter, the physician can move the tool shaft 328 axially over the surface of the cone-shaped recess 340 and into and through the working channel 175. By using this method, the physician can be assured that the tool shaft 328 will not contact the non-sterile field 320. In FIGS. 4 and 5, it can be seen that the proximal slanted surface 342 of the hub 176 is substantially in the same plane P (FIG. 4) as the surface 349 of the angled grip portion 182. It should be appreciated that a slanted surface 342' of the hub 176 can be provided in a plane outward from the surface 349 of the grip 182 to provide further assurance that the tool shaft 328 will not contact the non-sterile field 320.

Base Unit and Fluid Management System

Figure 10:
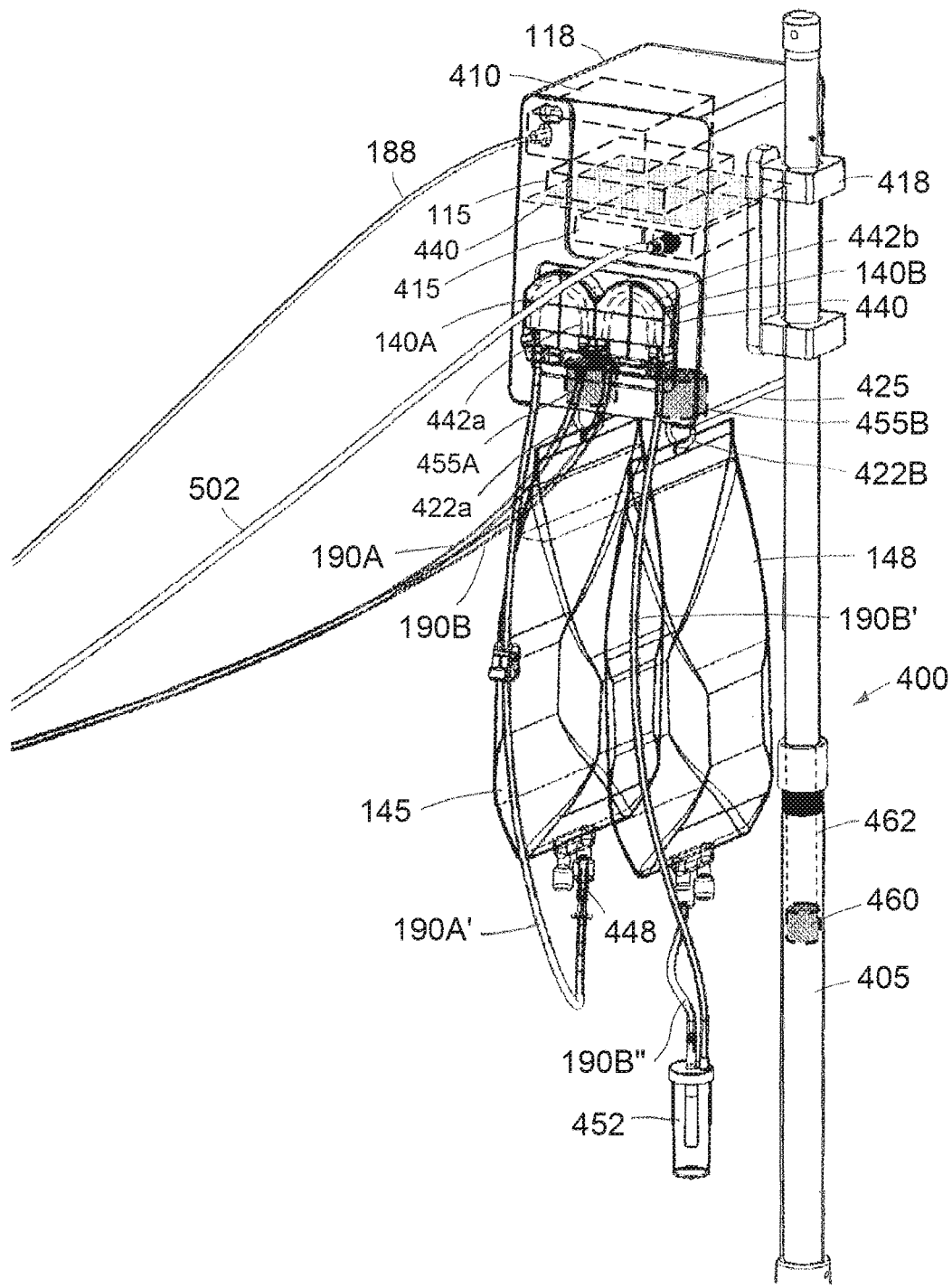
FIG. 10 is a perspective view of components of the fluid management system of FIG. 1A.

Now turning to FIGS. 1A and 10, the fluid management system 105 can be described in more detail. A rolling stand assembly 400 is provided which includes a base 402 with wheels 404 and a vertical pole assembly indicated at 405. The video display 320 is mounted at the top of the pole assembly 405. A controller base unit or base station 118 is attached to the pole assembly 405 which comprises a housing which contains the system controller 115, a video processor 410 and a 3-phase motor controller/power supply 415 for the resecting device 110 in this motor drive. Further, the base unit 118 carries the inflow and outflow peristaltic pumps 140A and 140B. The controller 115, as the term is used herein, includes processors or controller components for operating the fluid management system 105, the resecting device 110 and all aspects of the endoscopic viewing system 100. The base unit 118 also contains power supplies from the resecting device 110, the fluid management system 105 and the endoscopic viewing system 100.

As can be seen in FIG. 10, the base unit 118 is carried by a bracket 418 that secures the unit to the pole assembly 405. A fluid source, such as a 1-liter saline bag 145 is hung from a first hook 422a on the inferior surface 424 of the base unit 118. Further, another saline bag or collection reservoir 148 hangs from a second hook 422b on the inferior surface 425 of the base unit 118 for collecting fluid outflows.

FIGS. 1B and 10 further show a cassette 440 that carries first and second tubing loops 442a and 442b that are adapted to engage the roller assemblies of inflow and outflow pumps 140A and 140B. The cassette 440 shown in FIG. 11 includes a transducer membrane 444 (FIG. 1B) as is known in the art for interfacing with a pressure sensor and the surface of the control unit 118 that is engaged after the cassette 440 is locked in place.

In FIGS. 1A and 10, it can be seen that the inflow pump 140A pumps fluid through inflow tubing 190A to the endoscopic viewing component 100. FIG. 10 illustrates that a portion of the inflow tubing indicated at 190A' extends from the fluid source 145 to the tubing loop 442a in the cassette 440 that engages the inflow peristaltic pump 140A. The proximal end 448 of the inflow tubing portion 190A' as a spike for spiking the saline bag or fluid source 145 as is known in the art.

In FIGS. 1A and 10, it can be further seen that the outflow tubing 190B extends from the endoscopic viewing system 100 to the tubing loop 442b in the cassette 440 that engages the outflow peristaltic pump 140B. Beyond the tubing loop 445b in the cassette 440, an outflow tubing portion indicated at 190B' drops downward to a tissue trap 452 where tissue chips are filtered from the fluid outflow in collected. A second outflow tubing portion indicated that 190B" then extends upward to the collection reservoir 148.

Referring again to FIG. 10, the system includes at least one load sensor for providing weight signals to the controller indicating either the weight of the fluid in the inflow source 145 or the weight of the fluid in the collection reservoir 148 or the weight of the combined fluid inflow source 145 and collection reservoir 148. In one variation shown in FIG. 10, the first load cell 455a is shown with weighs fluid inflow source 145 in the second load cell 455b weighs the fluid collection reservoir. The controller 15 then can receive signals from the two load cells 455a and 455b to calculate the fluid loss. Further, the signal can be provided when a certain predetermined fluid loss has been observed. Also, the controller 115 can provide an alarm signal when the load so load cell 455a which weighs the fluid source 145 determines that the fluid source is rated a lower level, which may indicate that an additional saline bag be connected to the fluid management system.

Still referring to FIG. 10, in another variation, the weight management system can use a load cell 460 and the pole assembly 405 wherein telescoping shaft 462 can carry the weight of both the fluid inflow source 145 in the collection reservoir 148 and can be and continues the weigh the assembly in calculate the fluid deficit.

In another aspect of the invention, referring to FIG. 10, the base unit 118 is designed for use in a physician's office in therefore should be compact. In one variation the height of the base unit 118 is less than 18 inches, the width is less than 12 inches and the depth is less than 12 inches. Further, it has been found that the electrical interference caused by the 3-phase motor controller/power source 415 controller is substantial in the sensitivity of the video processor 410 is significant. Therefore, extensive electromagnetic shielding or EM shielding 488 is required between the 3-phase motor controller/power source and the video processor 410. In general, one aspect of the invention comprises providing a video processor within less than 12 inches from a three-phase motor power source and controller. In other variations, video processor is less than 8 inches, or less than 6 inches from the 3-phase motor controller/power source.

In general, as shown in FIG. 10, the base unit 118 includes a fluid management system 105 including inflow and outflow peristaltic pumps 140A and 140B, a cassette 440 carrying inflow and outflow tubing loops for engaging the inflow and outflow pumps, a coupled to the base unit 118 are a fluid source 145 comprising a first saline bag and a collection reservoir 148 comprising second saline bag. Further, the base unit 118 carries at least one load sensor intermediate the base unit housing in the first and second saline bag or weighing either or both of the first and second saline bags. A digital readout of the weight of either or both of the saline bag as is provided on the monitor 320 (FIG. 1A) for observation in the recording by the physician or nurse. By this means, the fluid deficit can be calculated.

In another variation, the inflow and outflow pumps of the fluid management system utilize encoder-type motors which can send signals relating to rotation to the controller 115. By this means, the controller 115 can calculate the volume of fluid inflows provided by a pump 140A into the working space in the patient's body. Thus, fluid inflows can be calculated either by a load cell or by signals from an encoder-type motor to the controller 115.

Tissue Resecting Device

Figure 11:
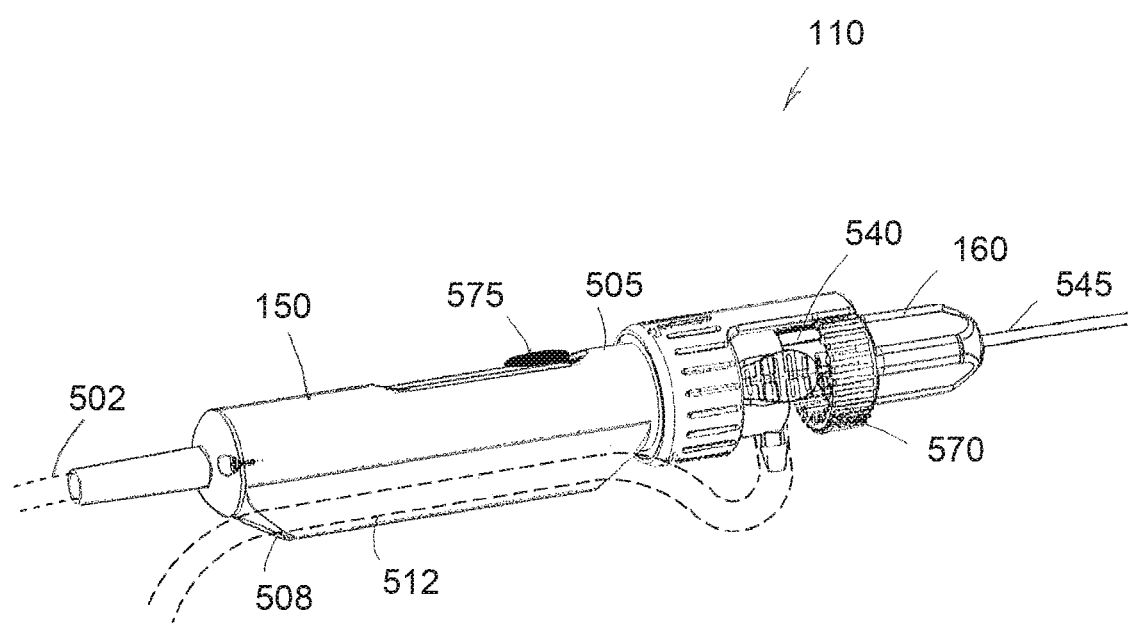
FIG. 11 is a perspective view of the handle portion of the resecting device of FIG. 1A showing the re-usable handpiece in the hub of the cutting component.
Figure 12:
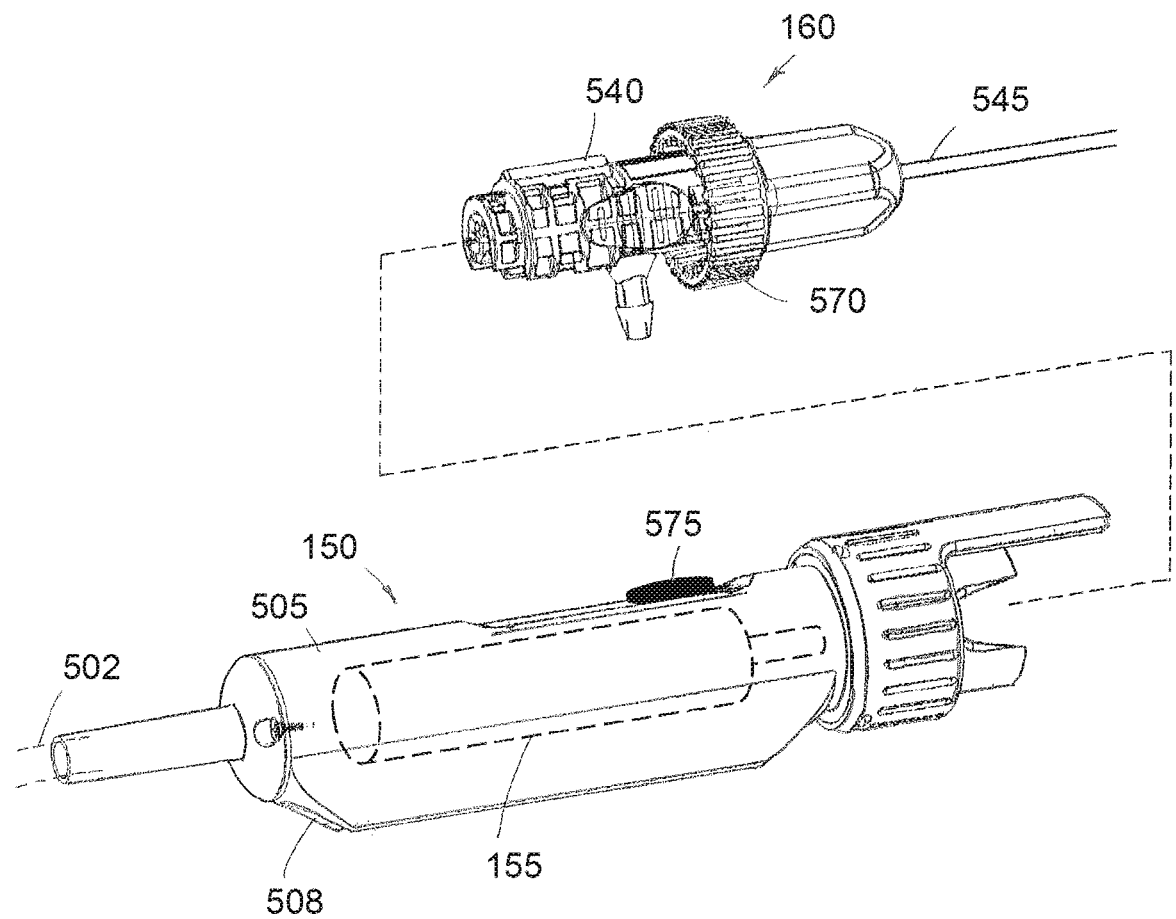
FIG. 12 is a view in the resecting device of FIG. 11 with the cutting component detached from the handpiece.

Now referring to FIGS. 1A, 11 and 12, the tissue resection device 110 comprises a re-usable handpiece 150 that carries a motor drive 155 together with the detachable cutting component 160. An electrical power cable 502 extends from the handpiece 150 to the 3-phase motor controller/power supply in the base unit 118. As can be seen in FIG. 11, the handpiece 150 has a housing 505 with a channel 508 in lower portion thereof to receive and lock therein the outflow tubing portion indicated at 512. In FIG. 1A, it can be seen that outflow tubing 512 extends to a branch connector 515 that couples tubing 512 to the outflow tubing 190B extending back to the outflow peristaltic pump 140B in the base unit 118. The outflow tubing 512 as shown in FIG. 1A is a pinch valve 518 for closing off the outflow tubing 512. In FIG. 1A, it can be understood that the primary outflow tubing 190A extends to the endoscopic viewing system 100 through the branch connector 515 into tubing portion 520 to the hub 176 of the endoscope component 125 as described above. Thus, the endoscopic viewing assembly 100 can be used for both inflows and outflows during insertion of the endoscope shaft assembly 162 into the patient, with the pinch valve 518 closing off the outflow tubing 512 since the resecting device 110 is not yet in use (FIG. 1A). After the endoscope shaft assembly 162 has been navigated to a working space in a patient's body, and the resecting device 110 has been introduced through the working channel 175 of the endoscope component 125, the pinch valve 518 can be opened so that fluid outflows are provided through the resecting device 110 rather than through the working channel 175 of the endoscope component 125.

Figure 13:
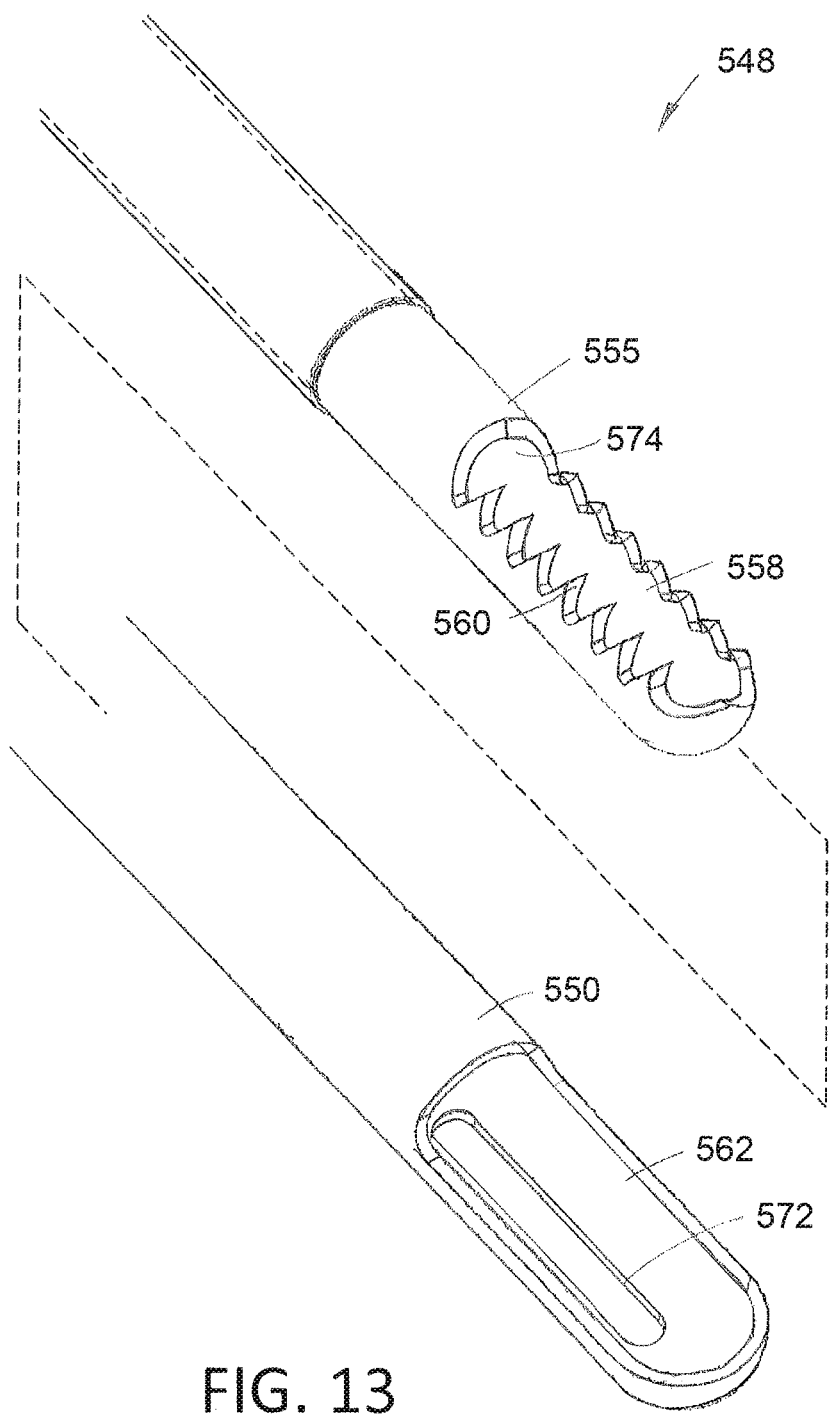
FIG. 13 is an enlarged perspective view of the working end of the resecting device of FIGS. 1A and 11 with the inner sleeve separated from the outer sleeve showing an aperture arrangement in the outer sleeve.

Now turning to FIG. 12, it can be seen that the cutting component 160 has a proximal hub 540 that is adapted for detachably coupling to the handle 150. An elongated shaft assembly 545 extends distally from the hub 540 to a working end 548 (FIG. 1A). In one variation, elongated shaft assembly 545 comprises an outer sleeve 550 with a distal window 552 and a rotating inner sleeve 555 with a window 558 (FIG. 13). Such a type of tubular cutter is known in the art wherein the rotating inner sleeve 555 cuts tissue that interfaces with window 552 in the outer sleeve 550 as the inner sleeve window 558 with teeth 560 rotates at high speed.

As can be seen in FIGS. 11 and 12, the hub 540 of the resecting component 160 is coupled to a rotating collar 570 which is fixed to the shaft assembly 545 so that the physician can rotate the shaft assembly 545 and working end 548 to any rotational orientation for cutting tissue while maintaining the handle 150 in an upright position. The handle 150 includes an actuator button 575 for actuating the motor drive 155 to rotate the inner sleeve 555 relative to the outer sleeve 550 to thereby cut tissue.

Referring to FIG. 12, the tissue resecting device 110 can have a shaft assembly 5456 with a diameter ranging from 2 mm to 6 mm, in is more often between 3 mm and 5 mm. The shaft 545 has a diameter and length for cooperating with the working channel 175 of the endoscopic viewing system 100 as shown in FIG. 1A.

Now turning to FIG. 13, the distal working end 548 of the cutting component, and more particularly, the outer and inner sleeves, 550 and 555, are shown separated to show particular features that correspond to the invention. In FIG. 13, it can be seen that the outer sleeve 550 is in has an aperture arrangement or opening 572 in the surface that opposes the window 562. Typically, in a high-speed rotating tubular cutter that is used in hysteroscopy with a fluid management system, the motor controller includes algorithms for stopping rotation of the inner sleeve 555 relative to the outer sleeve 550 so that the windows 558 and 562 are aligned when the inner sleeve 555 stopped rotating. In such prior art devices, various sensors and mechanisms have been developed to stop rotation of the inner sleeve 555 in a predetermined position with the inner and outer windows 558, 562 being oriented to be at least partially aligned and open. Such algorithms are complex and may not function reliably in all operating environments. The reason for needing such a controller algorithm for stopping rotation of the inner sleeve 555 with windows 558 and 562 aligned is to ensure that the fluid management system continues to operate to maintain a set pressure in the body cavity when the resecting device is (i) operating at high speed or (ii) when the resecting device is paused in operation. The control algorithms of the fluid management system for maintaining a set pressure in a body cavity typically use a PID controller or a feedback control system as is known in the art. During operation of a resecting device with a rotating inner sleeve as shown in FIG. 13, the fluid management system controller can continuously monitor fluid outflows through the windows 558 and 562 when aligned since the sleeves are only in a window-closed position for a very brief interval as the inner sleeve 555 rotates. The stop algorithm is then used to stop rotation of the inner sleeve 555 in a window-open position and the controller again will monitor continuous fluid flows through the system to maintain the set pressure. However, if the inner sleeve 555 stopped rotating in a window-closed position, the actual pressure in the body cavity would immediately increase and the control algorithm could react by slowing or stopping the pumps but with no fluid outflows in the window-closed position, the PID controller could not operate which could increase actual pressure in the body cavity to an unsafe level or cause significant fluctuations in pressure in the working space when the resecting device is re-activated to provide fluid outflows.

In one aspect of the present invention, an opening or aperture arrangement 572 is disposed in a wall of outer sleeve 550 opposing the open window 562. In general, the opening 572 allows for outflows through the lumen 574 in the inner sleeve when it stops in the window closed position. Thus, providing an outflow opening 572 in the outer sleeve was the fluid management control system and PID feedback controller to operate and maintain the set pressure no matter whether the inner sleeve 555 is stopped in a window-open position or window-closed position or any intermediate position. In order to provide adequate flow through the outflow opening 572 in the window-closed position, it has been found that the area of opening 572 should be at least 10% of the area of window 558 in outer sleeve and more often at least 20% of the area of the window 558 in outer sleeve 555. In a variation, the area of opening 572 is at least 30% of the area of window 558 in outer sleeve 555. In FIG. 13, the opening 572 in the outer sleeve 550 is shown as a single elongated shape, but it should be appreciated that the opening can comprise a plurality of openings which can be any shape such as elongated slot or slots, an oval shape, round openings or the like.

Figure 14A:
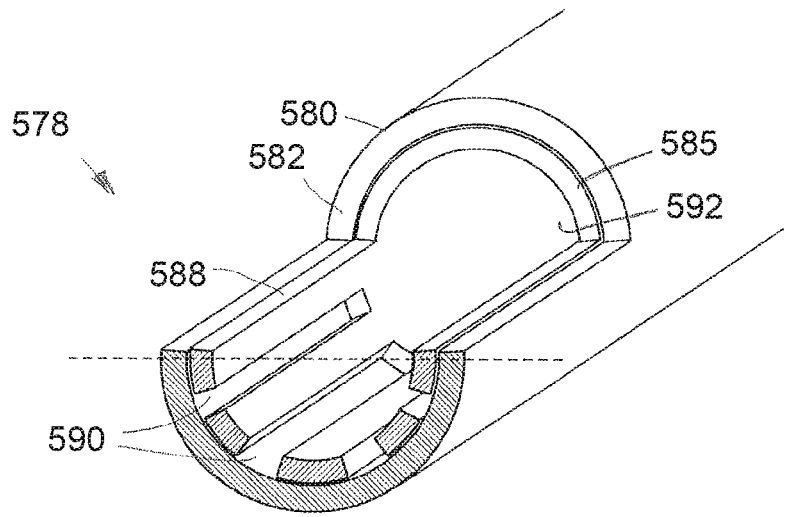
FIG. 14A is a schematic view of a working end of another resection device similar to that of FIGS. 1A and 11 showing an inner sleeve with a cutting window and opposing apertures in a first window-open position.
Figure 14B:
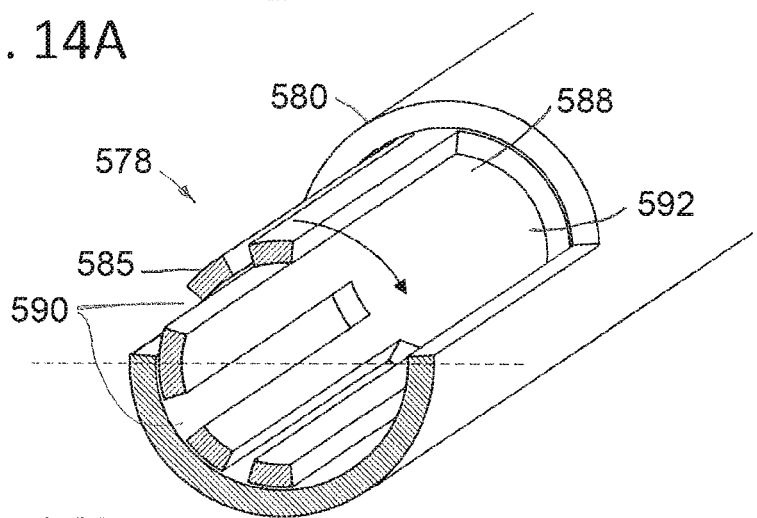
FIG. 14B is another view similar to that of FIG. 14A showing the inner sleeve and cutting window in a second position.
Figure 14C:
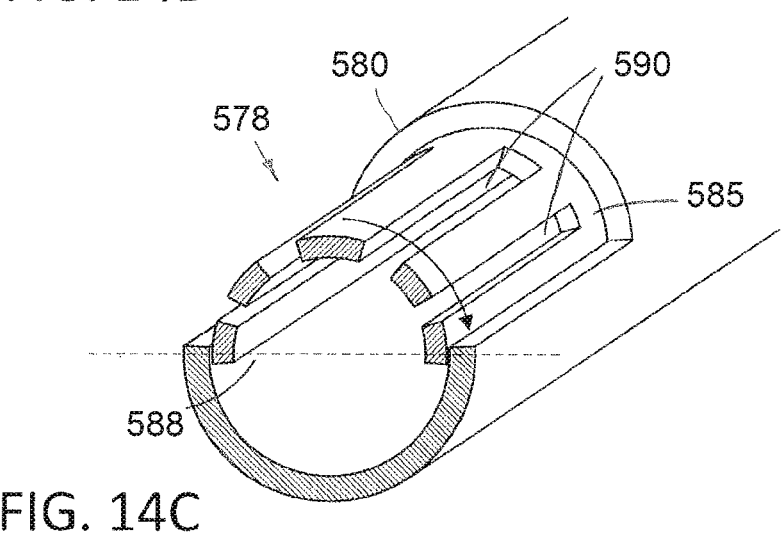
FIG. 14C is a view similar to that of FIGS. 14A-14B showing the inner sleeve and cutting window in a third window-closed position.

Now turning to FIGS. 14A to 14C, another variation of working end 578 is shown that is adapted to solve the same problem as the variation of FIG. 13. FIGS. 14A-14C are schematic views of a working end 578 of a tubular cutter with the outer sleeve 580 having window 582 therein. The inner sleeve 585 has cutting window 588 that for convenience is shown without cutting teeth. In this variation, it can be seen that inner sleeve 585 has a plurality of outflow openings 590 therein that extend longitudinally and are spaced apart around wall of the inner sleeve 585 opposing window 588. In this variation, the aperture arrangement can have from 1 to 20 or more openings. Again, it can be seen in FIG. 14C that when the working end 578 is in the window-closed position, the outflow openings 590 will still allow for fluid outflows through the interior channel 592 of the inner sleeve 585 to ensure that the PID controller or other control system still can function properly since there is a fluid flow through the device. The area of the apertures or openings again is greater than 10% of the outer sleeve window, greater than 20% or greater than 30% of the area of the window 582 in the outer sleeve 580.

In another aspect of the invention, the resecting device 110 comprises a tubular cutter wherein a windowed inner sleeve rotates relative to the outer sleeve between window-open in window-closed positions, and wherein a cooperating fluid management system provides of fluid outflows through a central channel in the tubular cutter and wherein the fluid outflow in the window-closed position is at least 10% of the fluid outflow through the tubular cutter in the window-open position under the same fluid management settings. Again, the fluid outflows in the window-closed position are provided through at least one aperture or opening in either the outer sleeve, the inner sleeve or combination of both the inner and outer sleeves. In another variation the fluid outflows in the window-closed position is at least 20% at least 30% of fluid outflows in the window-open position.

Referring to FIGS. 15A-15C, the working end 600 of another variation of a single-use endoscope 605 is shown wherein the proximal handle portion of the endoscope component (not shown) is the same as described previously. FIGS. 15A-15C illustrate the endoscope 600 again having a shaft assembly 610 with a straight proximal portion 612 that extends about a central longitudinal axis 615. In this variation, the shaft assembly 610 includes an articulating distal portion 620 that that can offset or displace the image sensor 622 from the longitudinal axis 615 to thus provide the configuration similar to earlier embodiments. As shown in FIG. 15A, the endoscope shaft assembly 610 can have a first straight cylindrical insertion profile 625 for introduction into a lumen in the patient's body, and a plurality of articulated or deflected profiles shown in FIGS. 15B and 15C. In this variation, the articulating distal portion 620 can comprise in thin-wall metal outer sleeve 628 surrounded by an elastomeric or flexible polymer sleeve 630. The articulating portion 620 can comprise a slotted region with first deflecting segment 632 and second deflecting segment 634 with deflectable slots 635 and 636. In FIG. 15B, it can be seen that the distal or first deflecting segment 632 of the articulating portion 620 has been deflected to thus alter the viewing angle VA of the image sensor 622 which is useful in a hysteroscopic procedure, for example, to view towards the fallopian tubes. FIG. 15C illustrates the second deflecting segment 634 of the articulating portion tips 620 after being articulated wherein the image sensor 622 again is oriented distally and generally in alignment with the axis 615 of the shaft assembly 610 except for the image sensor 622 has been moved radially outward to allow for introduction of a straight, rigid tool 640 through the working channel 644 of translatable inner sleeve 650 similar to previous embodiments. In this variation, the distal region 652 of the working channel 644 again includes the elastomeric portion 654 of the polymer sleeve 630 which allows the rigid tool 640 to be inserted through the endoscope shaft assembly 610.

Figure 18:
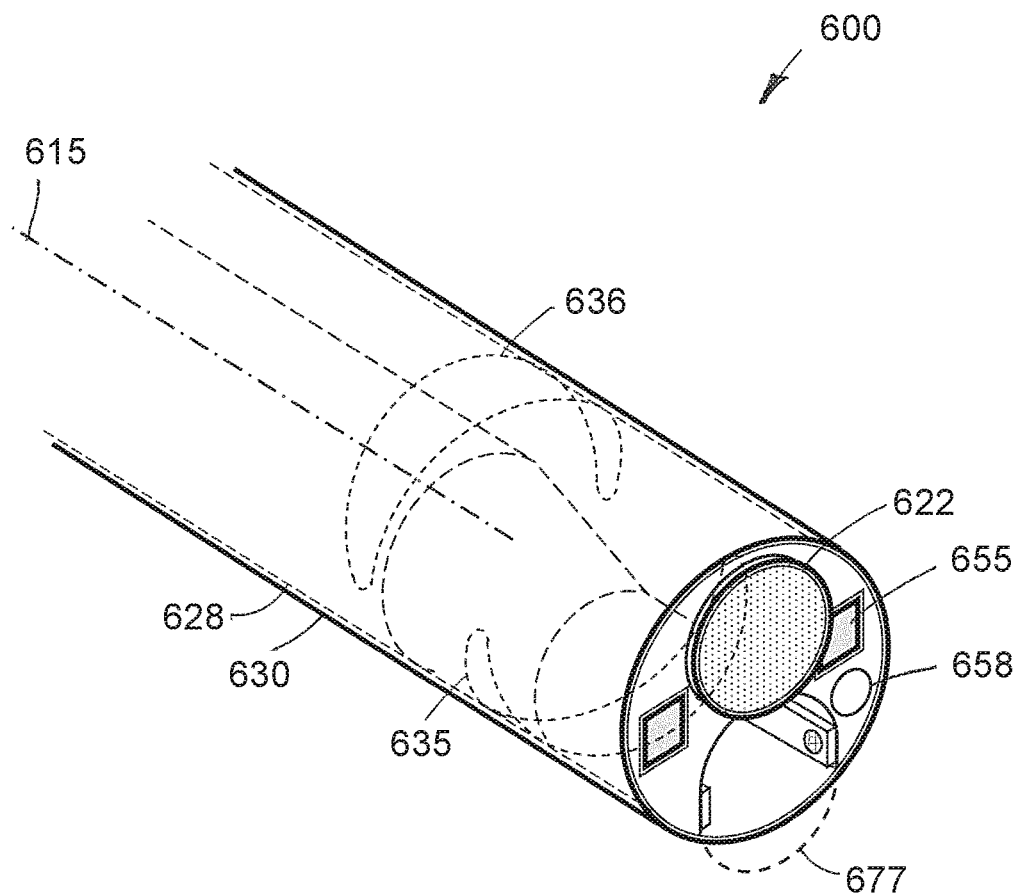
FIG. 18 is a perspective view of the working end of the endoscope of FIGS. 15A and 17A showing the LEDs and flow channels in the shaft assembly.

In the variation of endoscope 605 of FIGS. 15A-15C, the distal end of the endoscope shaft assembly 610 again includes LEDs 655 as shown in FIG. 18. Further, the endoscope shaft assembly 610 can again be configured with fluid inflow and outflow channels with one such flow channel 658 shown in FIG. 18. In one variation, the working channel 644 can be used for outflows and a second channel 658 is shown in FIG. 18 can be used for inflows, or vice versa. Another independent flow channel (not shown) can be provided for fluid communication with a pressure sensor if needed.

In FIGS. 15A to 15C, can be seen that the structural component of the shaft assembly 610 comprises the thin-wall metal sleeve 628 configured with slots or notches 635 and 636 for deflecting segments 632 and 634 as is known in the art of articulating shafts and endoscopes. While this variation includes only two slots 635 and 636 which allows for deflecting the two segments 632 and 634, it should be appreciated that the number of slots can range from 2 to 50 to provide the articulation or deflection as desired. In FIG. 15B, it can be seen that the distalmost or first segment 632 is articulated to change the viewing angle VA of the image sensor from 0° to about 15° relative to axis 615 for lateral viewing, but it should be appreciated that such the viewing angle in this deflected position can be altered anywhere from about 5° to 90° relative to axis 615.

In FIG. 15C, the second deflecting segment 634 of slotted sleeve 628 when deflected then displaces the image sensor 622 from its first position relative to axis 615 (FIG. 15A) to a second position that is radially outward relative to the axis 615 (FIG. 15C). As described previously, the outward displacement or position of the image sensor 622 allows for an expanding the cross-section of the working channel 644 in the distal end of the endoscope shaft assembly 610 to thus allow the rigid straight tool 640 to be introduced through the endoscope. At the same time, the image sensor viewing angle VA is oriented generally at 0° relative to the axis 615, although the viewing angle VA could be anywhere from 0° to 15° depending on the ultimate desired viewing angle. In any event, viewing angle VA in this position of the image sensor 622 in FIG. 15C is aligned for observing the working end of the tool 640, which typically is a resection device of the type described above.

It should be appreciated that articulating working ends of endoscopes and medical tools are well known in the art. Many such devices use concentric slotted tubes or pull-wires for providing articulation or deflection of such working ends. Now turning to FIGS. 16 and 17A, one variation of an articulation mechanism suitable for the endoscope of FIGS. 15A-15C is shown. In FIG. 17A, the endoscope working end 600 is shown with the outer elastomeric or flexible sleeve 630 shown in phantom view with the outer thin-wall metal sleeve 628 with slots 635 and 636 show more clearly. FIG. 17A also shows that the translatable or movable inner sleeve 650 is provided to articulate the distal articulating portion 620 of the endoscope working end 600. The inner sleeve 650 is shown in FIG. 16 independently from the shaft assembly 610 of FIG. 17A. As can be understood from FIGS. 16A-17, the interior lumen in the inner actuator sleeve 650 comprises the working channel 644. The inner sleeve 650 can be moved axially by any suitable mechanism in the handle, which can be a squeeze grip, a slider member or any other suitable finger-actuated mechanism (not shown). In FIG. 16, it can be seen that inner sleeve 650 has a distal portion with first and second extending elements 655a and 655a that are adapted to extend through the slotted segments 632 and 634 of the outer sleeve 628 (see FIG. 17A). In FIG. 17A, it can be seen that inner sleeve 650 extends through the shaft assembly 610 the distal tips 658a and 658b of the first and second extending elements 655a and 655b welded or otherwise fixed to the distal end 660 of the distal of first deflecting segment 632 with welds or pins 665. In FIGS. 16 and 17A, it can be seen that the first and second extending elements 655a, 655b also living hinge portion 670a and 670b that allow for flexing of the elements as the inner sleeve 650 is retracted or moved proximally to thereby articulate the working end 600.

Figure 17B:
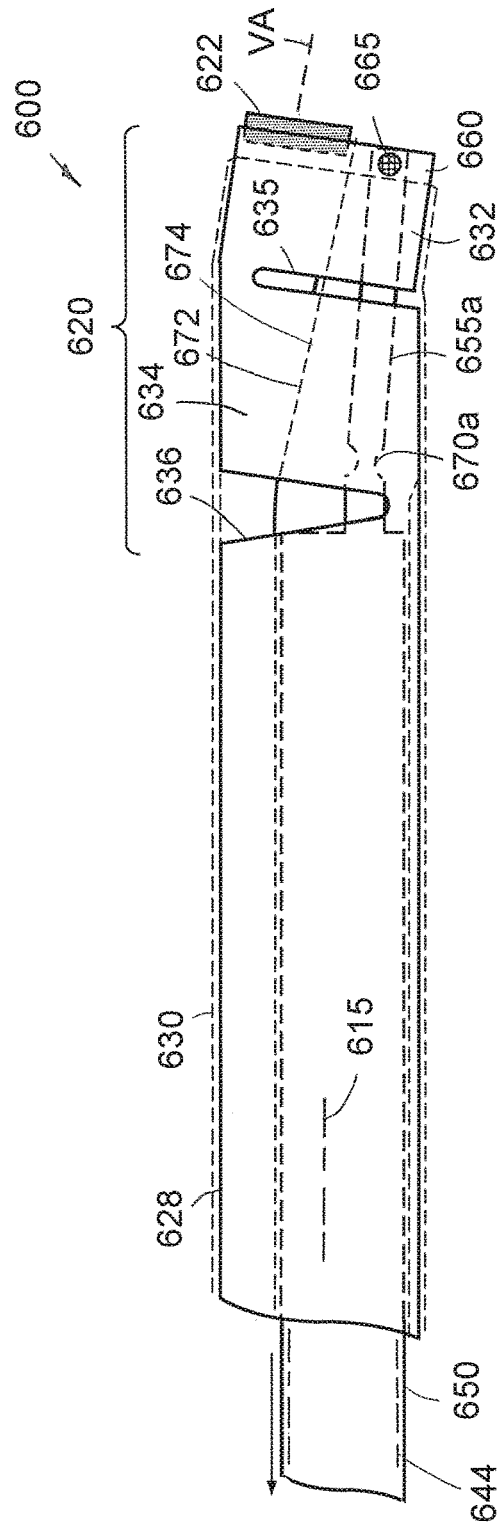
FIG. 17B is another view of the working end corresponding to FIG. 16B showing the outline of the actuator sleeve after retraction in the proximal direction to articulate the working end.

Now referring to FIG. 17B, which corresponds to the articulated configuration of FIG. 16B, it can be seen that the inner sleeve 650 is retracted in the proximal direction which then deflects the distalmost or first deflecting segment 632 of outer sleeve fluid and collapses the distal slot 635 to thereby alter the viewing angle VA of the image sensor 622 as described previously. In FIG. 17B, it can be seen that the distal extending elements 655a and 655b of inner sleeve 650 thus flex around the living hinge portion 670a and 670b is the sleeve 650 is retracted.

Figure 17C:
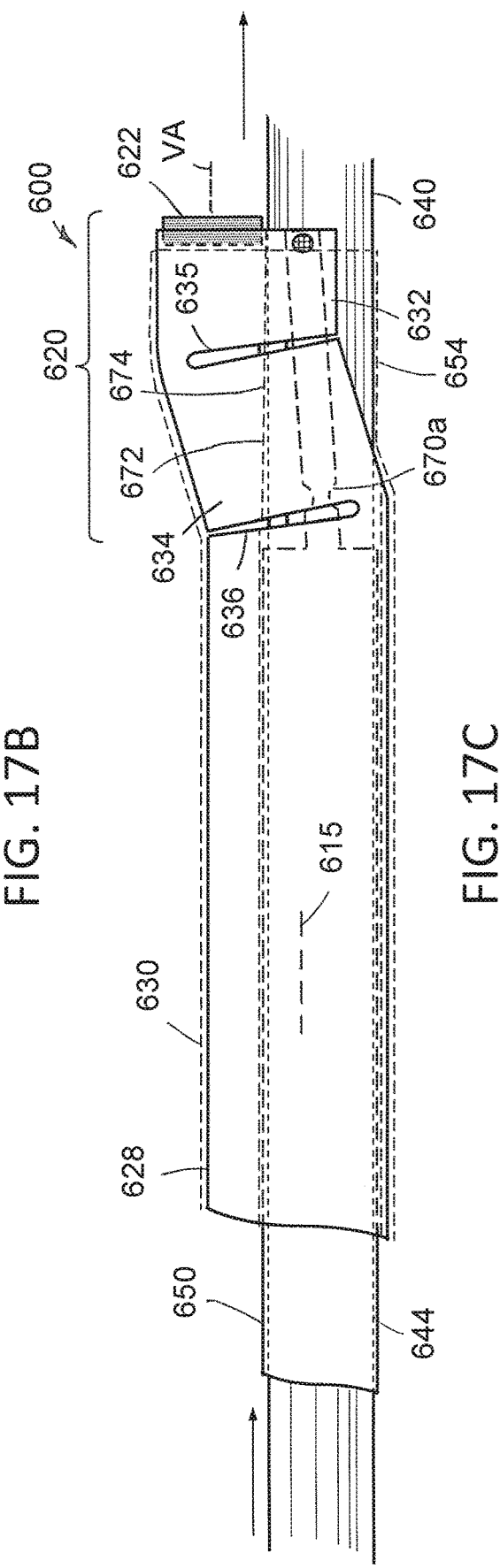
FIG. 17C is another view of the working end corresponding to FIG. 16C showing the outline of the actuator sleeve and the working end after the insertion of the rigid tool which further articulates the working end of the endoscope.

Now turning to FIG. 17C, the mechanism for further deflecting the working end 600 of the endoscope is shown. In FIG. 17C, the shaft of a straight rigid tool 640 is introduced through the working channel 644 in inner sleeve 650 wherein the tool 640 engages the superior surface 672 of the channel portion 674 within the second deflecting segment 634 and the first segment 632 of the slotted outer sleeve 628 to thereby deflect the distal working end 600 to this displace the image sensor 622 radially outward to a displaced position (FIG. 17C) from its initial position in the endoscope's insertion profile (FIG. 17A). As described previously, in this configuration, viewing angle VA of the image sensor 622 is generally 0° relative to axis 615 or a selected angle ranging between 0° and 15° for viewing the working end of tool 640 during a therapeutic procedure such as tissue resection. In FIG. 17C, it can be seen that the first and second extending elements 655a and 655b of the inner sleeve 650 again flex around the living hinge elements 670a and 670b.

In another variation (not shown), it should be appreciated that a pull-wire could be provided in used to articulate the second deflecting segment 634 of the outer sleeve 628 endoscope from the configuration of FIG. 17B to the configuration of FIG. 17C, as is known in the art. However, the use of the rigid tool 640 to deflect the working end 600 of endoscope simplifies the articulation mechanism by not requiring an additional actuator mechanism extending the shaft assembly 610 to the handle (not shown) of the endoscope.

As can be understood from FIGS. 16C and 17C, the flexible or elastomeric sheath 630 that encases the working end 600 of endoscope 605 has a distal portion 654 that is stretched outwardly to allow the rigid, straight tool 640 to be introduced through the working channel 644. FIG. 18 shows the working end 600 of the endoscope shaft assembly 610 assembly in a perspective view where again it can be seen that the flexible or elastomeric sleeve 630 is flexible and can be stretched outwardly as indicated by the dashed line 677 by the insertion of the tool 640 through the working channel 644.

In another variation (not shown), it should be appreciated that a pull-wire or other mechanism can be provided to initially articulate the second deflecting segment 634 the slotted outer sleeve 628 to thus deflect the image sensor 622 to provide a different viewing angle VA for lateral viewing. In such a variation, another mechanism can be used to deflect the first deflecting segment 632 of the slotted sleeve 628 to re-orient the image sensor 622 to the position of FIGS. 16C and 17C to providing suitable viewing angle in alignment with the axis 615 of shaft assembly 610 to allow for observation of the working end of the tool 640 during a therapeutic procedure.

As can be understood from FIGS. 15A-18, the endoscope shaft assembly 610 again allows for a working channel 644 that has a diagonal or diameter DW (see FIG. 15C, 16C) that is at least 50% of the diameter or diagonal of the shaft assembly 610 or insertion profile 625 (see FIG. 15A) and often the diameter DD may be 60% or more of the insertion profile. At the same time, the diagonal of the image sensor 622 can be at least 50% of the diameter or diagonal of the shaft assembly 610. Thus, the use of the articulating working end 600 allows for reorientation of the image sensor 622 to provide a plurality of viewing angles while the same time allowing a substantially small insertion profile 625 and large diagonal's of both the working channel 644 in the image sensor 622. As can be easily understood, the use of a "large-diagonal" image sensor allows for use of much higher resolution sensors to greatly increase the quality of the video images provided by the system and observed by the physician during a therapeutic procedure.

For example, in one variation the diameter of the endoscope's insertion profile can be in the range of 6.0 to 7.0 mm, the diameter of the working channel 644 can be 4.5 to 5.0 mm in the diagonal of the image sensor 622 can 4.0 to 5.0 mm.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. An endoscope used for insertion into a patient's body, the endoscope comprising:
    an outer sleeve defining a longitudinal axis, the outer sleeve comprising a first deflecting segment and a second deflecting segment at a distal portion of the outer sleeve, the outer sleeve comprising one or more slots at the distal portion;
    an inner sleeve positioned within the outer sleeve and comprising a working channel, the inner sleeve comprising one or more extending elements at a distal portion of the inner sleeve; wherein the one or more extending elements are coupled to the first deflecting segment of the outer sleeve;
    a tool advanceable through the working channel, wherein advancement of the tool transitions the distal portion of the outer sleeve between a straight profile and a deflected profile;
    wherein the distal portion of the outer sleeve is at an angle to the longitudinal axis in the deflected profile.

2. The endoscope of claim 1, further comprising a flexible polymer sleeve positioned around the outer sleeve.

3. The endoscope of claim 1, wherein the one or more extending elements each comprise a living hinge towards a proximal end of each of the one or more extending elements, wherein the living hinge is configured to flex the inner sleeve upon retraction of the inner sleeve.

4. The endoscope of claim 1, wherein the one or more extending elements each comprise a distal tip towards a distal end of each of the one or more extending elements, wherein the distal tip is coupled to the outer sleeve.

5. The endoscope of claim 4, wherein the distal tip is coupled to the outer sleeve via welding.

6. The endoscope of claim 4, wherein the distal tip is coupled to the outer sleeve via pins.

7. The endoscope of claim 1, further comprising image sensor at a distal end of the outer sleeve, wherein a viewing angle of the image sensor is parallel with respect to the longitudinal axis in the straight profile, wherein the viewing angle of the image sensor is angled with respect to the longitudinal axis in the deflected profile.

8. The endoscope of claim 7, wherein the viewing angle in the deflected profile is between 0 to 15 degrees.

9. The endoscope of claim 1, wherein the one or more slots or comprises a proximal slot and a distal slot, wherein deflection of the proximal slot is independent of deflection of the distal slot.

10. The endoscope of claim 1, further comprising a plurality of flow channels within the outer sleeve.

11. The endoscope of claim 10, further comprising a fluid inflow source communicating with the plurality of flow channels.

12. The endoscope of claim 10, further comprising a negative pressure source communicating with the plurality of flow channels.

13. The endoscope of claim 10, wherein a diameter of the working channel is at least 50% of a diameter of the distal portion of the outer sleeve.

* * * * *